US009414594B2

(12) United States Patent
Yang et al.

(10) Patent No.: US 9,414,594 B2
(45) Date of Patent: Aug. 16, 2016

(54) PROCESSES FOR THE PREPARATION OF PESTICIDAL COMPOUNDS

(71) Applicant: Dow AgroSciences LLC, Indianapolis, IN (US)

(72) Inventors: Qiang Yang, Zionsville, IN (US); Beth Lorsbach, Indianapolis, IN (US); Gregory Whiteker, Carmel, IN (US); Gary Roth, Midland, MI (US); Carl DeAmicis, Indianapolis, IN (US); Daniel I. Knueppel, Zionsville, IN (US); Ann M. Buysse, Carmel, IN (US); Kaitlyn Gray, Freeland, MI (US); Xiaoyong Li, Midland, MI (US); Joseck M. Muhuhi, Midland, MI (US); Ronald Ross, Jr., Zionsville, IN (US); David E. Podhorez, Midland, MI (US); Yu Zhang, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/715,956

(22) Filed: May 19, 2015

(65) Prior Publication Data
US 2015/0250177 A1 Sep. 10, 2015

Related U.S. Application Data

(62) Division of application No. 14/517,591, filed on Oct. 17, 2014, now Pat. No. 9,108,946.

(60) Provisional application No. 62/042,554, filed on Aug. 27, 2014, provisional application No. 61/892,129, filed on Oct. 17, 2013.

(51) Int. Cl.
*C07D 401/04* (2006.01)
*A01N 43/56* (2006.01)

(52) U.S. Cl.
CPC .............. *A01N 43/56* (2013.01); *C07D 401/04* (2013.01)

(58) Field of Classification Search
CPC .................................................... C07D 401/04
USPC .................................................... 546/275.4
See application file for complete search history.

(56) References Cited

U.S. PATENT DOCUMENTS

| | | |
|---|---|---|
| 3,597,341 A | 9/1968 | Alexis |
| 4,080,457 A | 3/1978 | Harrison et al. |
| 4,260,765 A | 4/1981 | Harrison et al. |
| 4,407,803 A | 10/1983 | Haviv et al. |
| 4,536,506 A | 8/1985 | Marcoux et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger et al. |
| 7,192,906 B2 | 3/2007 | Hirohara et al. |
| 7,196,104 B2 | 3/2007 | Askew, Jr. et al. |
| 7,319,108 B2 | 1/2008 | Schwink et al. |
| 7,774,978 B2 | 8/2010 | Ding et al. |
| 7,803,832 B2 | 9/2010 | Critcher et al. |
| 7,910,606 B2 | 3/2011 | Nazare et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |
| 9,044,017 B2 | 6/2015 | Yang et al. |
| 9,085,552 B1 | 7/2015 | Li et al. |
| 9,085,564 B2 | 7/2015 | Yang et al. |
| 9,102,654 B2 | 8/2015 | Yang et al. |
| 9,102,655 B2 | 8/2015 | Yang et al. |
| 9,108,932 B2 | 8/2015 | Ross et al. |
| 9,108,946 B2 | 8/2015 | Yang et al. |
| 9,115,115 B1 | 8/2015 | Yang et al. |
| 9,126,974 B2 | 9/2015 | Yang et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |

(Continued)

FOREIGN PATENT DOCUMENTS

| | | |
|---|---|---|
| EP | 0097323 | 1/1984 |
| EP | 0205024 | 12/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.

(Continued)

*Primary Examiner* — Patricia L Morris
(74) *Attorney, Agent, or Firm* — Carl D. Corvin; Barnes & Thornburg LLP

(57) ABSTRACT

The present application provides processes for making pesticidal compounds and compounds useful both as pesticides and in the making of pesticidal compounds.

5 Claims, No Drawings

(56) References Cited

U.S. PATENT DOCUMENTS

| | | |
|---|---|---|
| 2004/0043904 A1 | 3/2004 | Yamaguchi et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1* | 12/2013 | Numata ............... C07D 401/14 546/193 |

FOREIGN PATENT DOCUMENTS

| | | |
|---|---|---|
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1988-174905 | 7/1968 |
| JP | 1987-153273 | 7/1987 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2008/090382 | 7/2008 |
| WO | 2011/045224 | 10/2009 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/052412 | 4/2012 |
| WO | 2012/061290 | 5/2012 |
| WO | 2012/102387 | 8/2012 |
| WO | 2012/108511 | 8/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2012/035011 | 3/2013 |
| WO | 2012/070114 | 5/2013 |
| WO | 2013/062980 | 5/2013 |
| WO | 2013/062981 | 5/2013 |
| WO | 2013/156431 | 10/2013 |
| WO | 2013/156433 | 10/2013 |

OTHER PUBLICATIONS

Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.

Bradbury et al., "Enzyme-catalysed peptide amidation," Eur. J. Biochem. 1987, vol. 169, pp. 579-584.

International Search Report and Written Opinion for PCT/US2014/061005 mailed Dec. 16, 2014.

International Search Report and Written Opinion for PCT/US2014/061006 mailed Dec. 8, 2014.

International Search Report and Written Opinion for PCT/US2014/061007 mailed Dec. 31, 2014.

International Search Report and Written Opinion for PCT/US2014/061009 mailed Dec. 8, 2014.

(56) References Cited

OTHER PUBLICATIONS

International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 mailed Dec. 21, 2012.
International Search Report and Written Opinion for PCT/US2011/058578 mailed Apr. 5, 2012.

* cited by examiner

PROCESSES FOR THE PREPARATION OF PESTICIDAL COMPOUNDS

CROSS REFERENCE TO RELATED APPLICATIONS

This Application is a divisional of U.S. application Ser. No. 14/517,591 filed on Oct. 17, 2014, which claims the benefit of the following U.S. Provisional Patent Applications: Ser. No. 62/042,554 filed Aug. 27, 2014; and Ser. No. 61/892,129 filed Oct. 17, 2013, the entire disclosures of which are hereby expressly incorporated by reference into this Application.

TECHNICAL FIELD

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioether and pesticidal sulfoxides efficiently and in high yield from commercially available starting materials.

DETAILED DESCRIPTION

The following definitions apply to the terms as used throughout this specification, unless otherwise limited in specific instances.

As used herein, the term "alkyl" denotes branched or unbranched hydrocarbon chains.

As used herein, the term "alkynyl" denotes branched or unbranched hydrocarbon chains having at least one C≡C.

Unless otherwise indicated, the term "cycloalkyl" as employed herein alone is a saturated cyclic hydrocarbon group, such as cyclopropyl, cyclobutyl, cyclopentyl, cyclohexyl.

The term "thio" as used herein as part of another group refers to a sulfur atom serving as a linker between two groups.

The term "halogen" or "halo" as used herein alone or as part of another group refers to chlorine, bromine, fluorine, and iodine.

The pesticidal thioethers of formula 3c (3c)

and the pesticidal sulfoxides of formula 3d (3d)

wherein,
$R^1$ is selected from the group consisting of $C_1$-$C_4$-haloalkyl and $C_1$-$C_4$-alkyl-$C_3$-$C_6$-halocycloalkyl, and
$R^2$ is selected from the group consisting of $C_1$-$C_4$-alkyl and $C_2$-$C_4$-alkynyl can be prepared by the methods illustrated in Schemes 1 to 9.

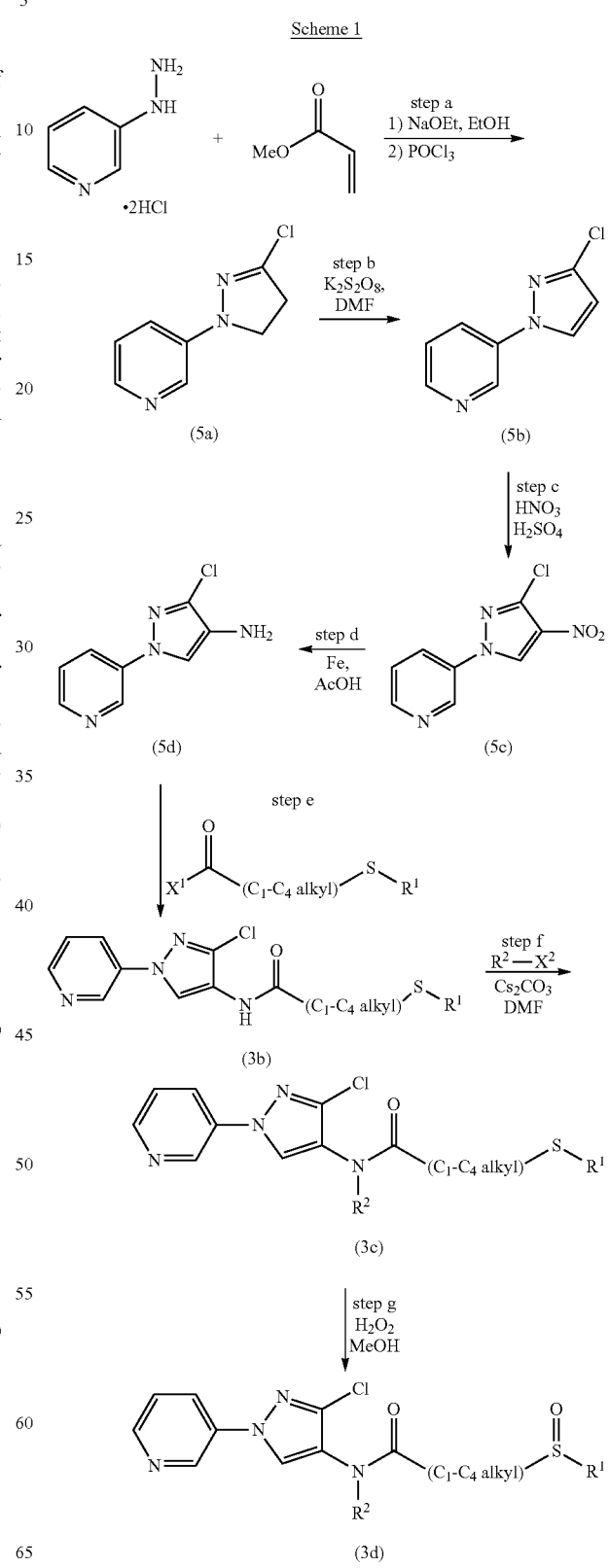

Scheme 1

In step a of Scheme 1, 3-hydrazinopyridine dihydrochloride is reacted with methyl acrylate in the presence of a base such as sodium methoxide or sodium ethoxide to yield 1-(pyridin-3-yl)pyrazolidin-3-one followed by chlorination of 1-(pyridine-3-yl)pyrazolidin-3-one with phosphoryl chloride (POCl$_3$) in a two-step process to yield dihydropyrazole chloride (5a). The first step may be conducted in a polar protic solvent such as, methanol (MeOH) or ethanol (EtOH), at a temperature from about 40° C. to about 80° C. The second step may be conducted neat in phosphoryl chloride at a temperature from about 40° C. to about 80° C. When the crude product from the first step was neutralized, the second step can also be conducted in a solvent like acetonitrile (MeCN) at a temperature from about 40° C. to about 80° C.

In step b of Scheme 1, 3-(3-chloro-4,5-dihydro-1H-pyrazol-1-yl)pyridine (5a) is reacted with an oxidant to yield 3-(3-chloro-1H-pyrazol-1-yl)pyridine (5b). The oxidation may be conducted with potassium persulfate (K$_2$S$_2$O$_8$) in N,N-dimethylformamide (DMF) at about 80° C. to yield the product (5b). The oxidation may be conducted with about 0.3 equivalents to about 0.5 equivalents of a copper(I) salt, such as copper(I) sulfate (Cu$_2$SO$_4$), or a copper(I) halide, such as copper(I) chloride (CuCl), in the presence of an oxygen source, such as air, in a polar aprotic solvent such as N,N-dimethylformamide, N-methylpyrrolidinone (NMP) or 1,4-dioxane at temperatures from about 25° C. to about 100° C. This procedure results in higher yields and is more selective for 3-(3-chloro-1H-pyrazol-1-yl)pyridine (5b).

In step c of Scheme 1, 3-(3-chloro-1H-pyrazol-1-yl)pyridine (5b) is nitrated with nitric (HNO$_3$) and sulfuric (H$_2$SO$_4$) acids to yield 3-(3-chloro-4-nitro-1H-pyrazol-1-yl)pyridine (5c). The nitration may be conducted at about −10° C. to about 30° C.

In step d of Scheme 1, compound (5c) is reduced to yield 3-chloro-1-(pyridin-3-yl)-1H-pyrazol-4-amine (5d). For example, compound (5c) may be reduced with iron in acetic acid (AcOH). Compound (5c) may also be reduced with iron and ammonium chloride (NH$_4$Cl). Alternatively, this reduction may occur using other techniques in the art, for example, compound (5c) may be reduced using palladium on carbon in the presence of hydrogen (H$_2$).

In step e of Scheme 1, 3-chloro-1-(pyridin-3-yl)-1H-pyrazol-4-amine (5d) is reacted with an activated carbonyl thioether, indicated as $X^1C(=O)C_1$-$C_4$-alkyl-S—$R^1$, to yield pesticidal thioether (3b). $R^1$ is selected from the group consisting of $C_1$-$C_4$-haloalkyl and $C_1$-$C_4$-alkyl-$C_3$-$C_6$-halocycloalkyl; preferably, $R^1$ is selected from CH$_2$CH$_2$CF$_3$ or CH$_2$ (2,2-difluorocyclopropyl). $X^1$ is selected from Cl, OC(=O) $C_1$-$C_4$ alkyl, or a group that forms an activated carboxylic acid. When $X^1$ is Cl or OC(=O)$C_1$-$C_4$ alkyl the reaction is conducted in the presence of a base, preferably sodium bicarbonate, to yield pesticidal thioether (3b). Alternatively, the reaction may be accomplished when $X^1C(=O)C_1$-$C_4$-alkyl-S—$R^1$ is an activated carboxylic acid activated by such reagents as 2,4,6-tripropyl-trioxatriphosphinane-2,4,-trioxide (T$_3$P), carbonyldiimidazole (CDI), dicyclohexylcarbodiimide (DCC) or 1-ethyl-3-(3-dimethylaminopropyl)carbodiimide (EDC), preferably 2,4,6-tripropyl-trioxatriphosphinane-2,4,-trioxide and carbonyldiimidazole at temperatures from about 0° C. to about 80° C.; this reaction may also be facilitated with uronium or phosphonium activating groups such as O-(7-azabenzotriazol-1-yl)-N,N,N',N'-tetramethyl-uronium hexafluorophosphate (HATU) or benzotriazol-1-yl-oxytripyrrolidinophosphonium hexafluorophosphate (PyBOP), in the presence of an amine base such as diisopropylethylamine (DIPEA) or triethylamine (TEA) in an polar aprotic solvent such as N,N-dimethylformamide, tetrahydrofuran (THF) or dichloromethane (CH$_2$Cl$_2$), at temperatures from about −10° C. to about 30° C. to form pesticidal thioether (3b). Activated carbonyl thioethers may be formed from carboxylic acids, indicated as $X^1C(=O)C_1$-$C_4$-alkyl-S—$R^1$, wherein $X^1$ is OH, which may be prepared by reacting the corresponding ester thioether, indicated as $X^1C(=O)C_1$-$C_4$-alkyl-S—$R^1$, wherein $X^1$ is OC$_1$-$C_4$-alkyl, with a metal hydroxide such as lithium hydroxide (LiOH) in a polar solvent such as methanol or tetrahydrofuran.

Alternatively, $X^1C(=O)C_1$-$C_4$-alkyl-S—$R^1$, wherein $X^1$ is OH or OC$_1$-$C_4$-alkyl may be prepared by the photochemical free-radical coupling of 3-mercaptopropionic acid and esters thereof with 3,3,3-trifluoropropene in the presence of 2,2-dimethoxy-2-phenylacetophenone initiator and long wavelength UV light in an inert organic solvent. While stoichiometric amounts of 3-mercaptopropionic acid or esters thereof and 3,3,3-trifluoropropene are required, because of its low boiling point, excess 3,3,3-trifluoropropene is usually employed to compensate for routine losses. From about 1 to about 10 mole percent initiator, 2,2-dimethoxy-2-phenylacetophenone, is typically used, with about 5 mole percent being preferred. Long wavelength UV light is sometimes called "black light" and ranges from about 400 to about 365 nanometers. The photochemical coupling is conducted in an inert organic solvent. Typical inert organic solvents must remain liquid to about −50° C., must remain relatively inert to the free radical conditions and must dissolve the reactants at reaction temperatures. Preferred inert organic solvents are aromatic and aliphatic hydrocarbons like toluene. The temperature at which the reaction is conducted is not critical but usually is from about −50° C. to about 35° C. Lower temperatures, however, are better for increased selectivity. Initially, it is important to keep the temperature below the boiling point of 3,3,3-trifluoropropene, i.e., about −18 to about −16° C. In a typical reaction, the inert organic solvent is cooled to less than about −50° C. and the 3,3,3-trifluoropropene is bubbled into the solvent. The 3-mercaptopropionic acid or esters thereof and 2,2-dimethoxy-2-phenylacetophenone are added and a long wave function (366 nm) UVP lamp (4 watt) is turned on. After sufficient conversion of 3-mercaptopropionic acid or esters thereof, the light is turned off and the solvent removed.

3-((3,3,3-Trifluoropropyl)thio)propanoic acid may also be prepared by the low temperature free-radical initiated coupling of 3-mercaptopropionic acid with 3,3,3-trifluoropropene in the presence of 2,2'-azobis(4-methoxy-2,4-dimethyl) valeronitrile (V-70) initiator at temperatures of about −50° C. to about 40° C. in an inert organic solvent. While stoichiometric amounts of 3-mercaptopropionic acid and 3,3,3-trifluoropropene are required, because of its low boiling point, excess 3,3,3-trifluoropropene is usually employed to compensate for routine losses. From about 1 to about 10 mole percent initiator, V-70, is typically used, with about 5 mole percent being preferred. The low temperature free-radical initiated coupling is conducted in an inert organic solvent. Typical inert organic solvents must remain liquid to about −50° C., must remain relatively inert to the free radical conditions and must dissolve the reactants at reaction temperatures. Preferred inert organic solvents are toluene, ethyl acetate, and methanol. The temperature at which the reaction is conducted from about −50° C. to about 40° C. Initially, it is important to keep the temperature below the boiling point of 3,3,3-trifluoropropene, i.e., about −18 to about −16° C. The solution is cooled to less than about −50° C. and the 3,3,3-trifluoropropene is transferred into the reaction mixture. After stirring at room temperature for 24 hours, the reaction mixture is heated to about 50° C. for about 1 hour to decompose any remaining V-70 initiator followed by cooling and solvent removal.

In step f of Scheme 1, pesticidal thioether (3b) is alkylated with a R²—X² to yield pesticidal thioether (3c), wherein X² is a leaving group. The leaving group may be selected from halo, mesylate, or tosylate. R² is selected from $C_1$-$C_4$-alkyl, $C_2$-$C_4$-alkynyl, preferably, methyl, ethyl, and propargyl. R²—X² may be selected from methyl iodide, ethyl bromide, ethyl iodide, propargyl chloride, propargyl bromide, ethyl mesylate, propargyl mesylate, ethyl tosylate and propargyl tosylate. The alkylation is conducted in the presence of an inorganic base, preferably, metal carbonates such as cesium carbonate ($Cs_2CO_3$), metal hydroxides, metal phosphates, metal hydrides, conducted in the presence of a polar solvent, such as N,N-dimethylformamide at temperature from about 0° C. to about 80° C.

Alternatively, in step f of Scheme 1, the alkylation of pesticidal thioether (3b) may be conducted in the presence of a base such as sodium hydride (NaH), in the presence of a polar aprotic solvent, such as N,N-dimethylformamide, tetrahydrofuran, hexamethylphosphoramide (HMPA), dimethylsulfoxide (DMSO), N-methyl-2-pyrrolidinone or sulfolane, at temperatures from about 0° C. to about 30° C. It has been unexpectedly discovered that the use of sulfolane as solvent promotes the alkylation reaction over the competitive retro-Michael-type elimination of the $C_1$-$C_4$-alkyl-S—R¹ unit (see "CE-6"). It has been discovered that the catalytic use of an iodide additive, such as potassium iodide (KI) or tetrabutylammonium iodide (TBAI) decreases the time necessary for the reaction to occur to about 24 hours.

In step g of Scheme 1, pesticidal thioether (3c) is oxidized with hydrogen peroxide ($H_2O_2$) in methanol to yield pesticidal sulfoxides (3d).

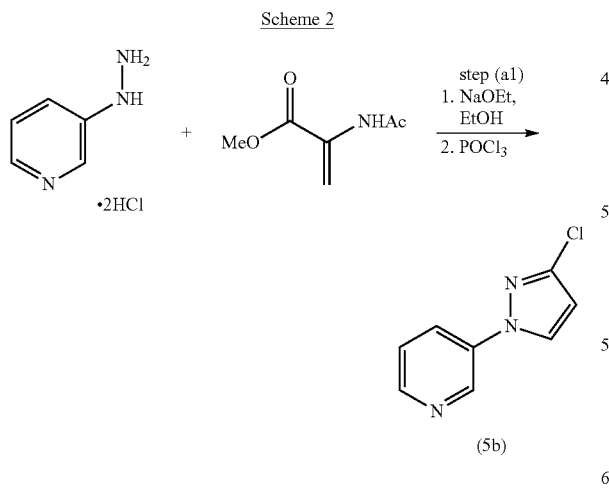

3-(3-Chloro-1H-pyrazol-1-yl)pyridine (5b) in Scheme 1 may alternatively be prepared by reacting 3-hydrazinopyridine dihydrochloride with methyl 2-acetamidoacrylate to yield N-(3-oxo-1-(pyridin-3-yl)pyrazolidin-4-yl)acetamide and subsequent chlorination/elimination as shown in Scheme 2, step a1.

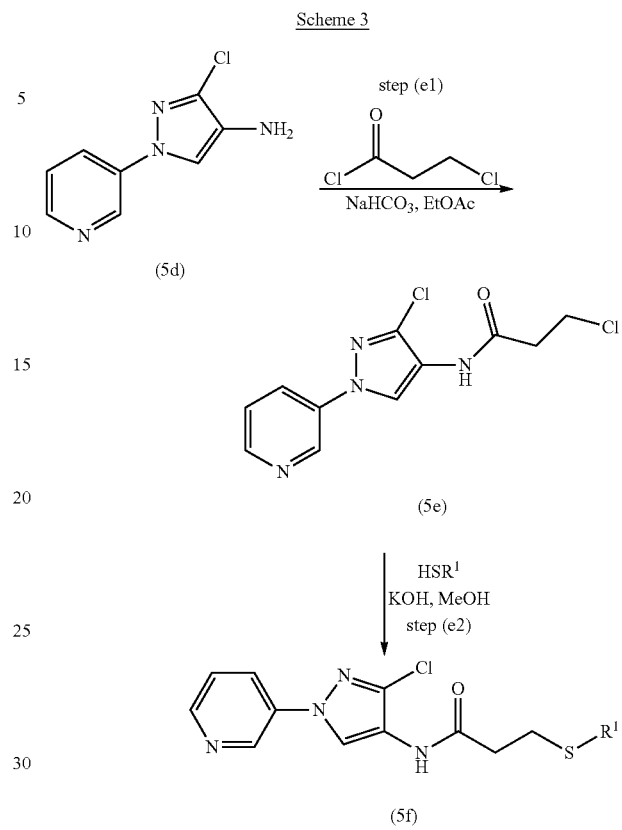

Pesticidal thioether (5f) may be prepared from amine (5d) through the reaction pathway disclosed in Scheme 3. In step e1 of Scheme 3, 3-chloro-N-ethyl-1-(pyridin-3-yl)-1H-pyrazol-amine (5d) is reacted with between about 1 equivalent and about 2 equivalents of 3-chloropropionyl chloride in the presence of an inorganic base, preferably, metal carbonates, metal hydroxides, metal phosphates, metal hydrides, more preferably sodium bicarbonate ($NaHCO_3$) to yield 3-chloro-N-(3-chloro-1-(pyridin-3-yl)-1H-pyrazol-4-yl)-N-ethylpropanamide (5e).

In step e2 of Scheme 3, compound (5e) reacts with HSR¹, wherein R¹ is defined above, in the presence of an inorganic base, preferably, metal carbonates, metal hydroxides, metal phosphates, metal hydrides, more preferably, potassium hydroxide (KOH). This reaction may be conducted in the presence of a polar solvent, preferably methanol, to yield pesticidal thioether (5f).

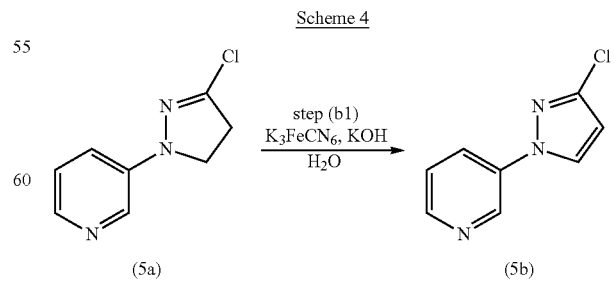

3-(3-Chloro-1H-pyrazol-1-yl)pyridine (5b) may be prepared through the reaction pathway disclosed in Scheme 4. In step b1, 3-(3-chloro-4,5-dihydro-1H-pyrazol-1-yl)pyridine (5a) is reacted with an oxidant to yield 3-(3-chloro-1H-pyrazol-1-yl)pyridine (5b). The oxidation may be conducted with about 2 equivalents to about 4 equivalents of potassium ferricyanide ($K_2FeCN_6$) in water in the presence of about 2 equivalents to about 20 equivalents of an alkali metal base, such as potassium hydroxide, sodium hydroxide, or potassium carbonate, at temperatures ranging from about 50° C. to about 100° C. to yield the product (5b). About 1.5 equivalents to 3.0 equivalents potassium persulfate can be added as a terminal oxidant in this oxidation. The amount of potassium ferricyanide can then be lowered to 1 equivalent with improved yield.

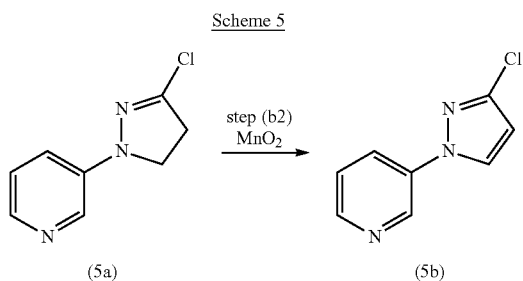 [SMILES: ClC1=NN(c2cccnc2)CC1 ; Clc1ccn(-c2cccnc2)n1]

Scheme 5

3-(3-Chloro-1H-pyrazol-1-yl)pyridine (5b) may be prepared through the reaction pathway disclosed in Scheme 5. In step b2, 3-(3-chloro-4,5-dihydro-1H-pyrazol-1-yl)pyridine (5a) is reacted with an oxidant to yield 3-(3-chloro-1H-pyrazol-1-yl)pyridine (5b). The oxidation may be conducted with about 1.5 equivalents to about 10 equivalents of manganese (IV) oxide ($MnO_2$) in a solvent such as acetonitrile, tert-amyl alcohol, or chlorobenzene, at temperatures ranging from about 60° C. to about 90° C. to yield the product (5b). Subsequent treatment of (5b) with a strong acid such as hydrochloric acid (HCl) may provide the salt of the product (5b).

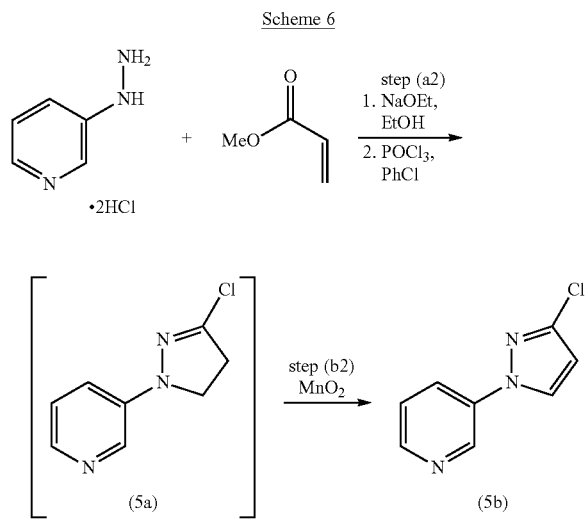

Scheme 6

3-(3-Chloro-1H-pyrazol-1-yl)pyridine (5b) may also be prepared through a three step, no isolation reaction sequence as disclosed in Scheme 6. In step a2, 3-hydrazinopyridine dihydrochloride is reacted with methyl acrylate in the presence of a base such as sodium methoxide or sodium ethoxide to yield 1-(pyridin-3-yl)pyrazolidin-3-one, followed by chlorination of 1-(pyridine-3-yl)pyrazolidin-3-one with phosphoryl chloride in a two-step process to yield 3-chloro-dihydropryazole (5a). In step b2, 3-(3-chloro-4,5-dihydro-1H-pyrazol-1-yl)pyridine (5a) is reacted with manganese (IV) oxide to yield the product (5b). Subsequent treatment of (5b) with an acid such as hydrochloric acid may provide the salt of the product (5b). The first step may be conducted in a polar protic solvent such as methanol or ethanol, at a temperature from about 40° C. to about 80° C. The second step may be conducted in a solvent such as chlorobenzene at a temperature from about 70° C. to about 90° C. The third step may be conducted in a solvent such as chlorobenzene at a temperature from about 70° C. to about 110° C.

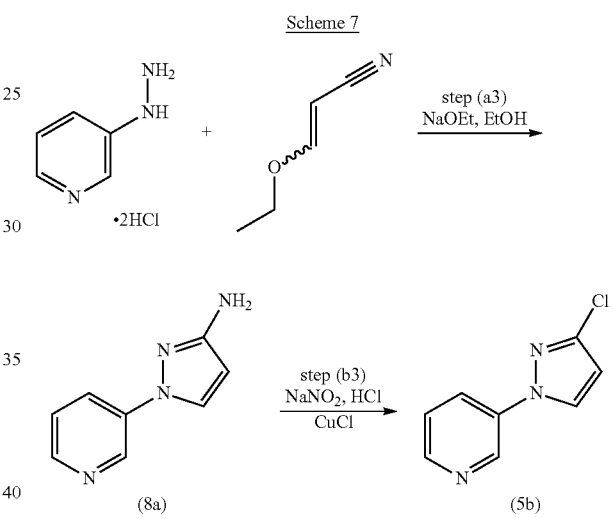

Scheme 7

3-(3-Chloro-1H-pyrazol-1-yl)pyridine (5b) may also be prepared through a two-step reaction sequence as disclosed in Scheme 7. In step a3, 3-hydrazinopyridine.dihydrochloride is reacted with 3-ethoxyacrylonitrile or 3-methoxyacylonitrile in the presence of an alkali metal $C_1$-$C_4$ alkoxide base such as sodium methoxide (NaOMe) or sodium ethoxide (NaOEt) to yield 3-(3-amino-1H-pyrazol-1-yl)pyridine (8a). In step b3, 3-(3-amino-1H-pyrazol-1-yl)pyridine (8a) is reacted with sodium nitrite ($NaNO_2$) in aqueous hydrochloric acid to provide the corresponding diazonium salt followed by treatment of the diazonium salt with copper chloride to yield the product (5b). The first step may be conducted in a $C_1$-$C_4$ aliphatic alcohol solvent such as methanol or ethanol, at a temperature from about 25° C. to about 100° C. It is most convenient that the alkoxide base and the alcohol solvent be the same, for example, sodium ethoxide in ethanol. The second step may be conducted at a temperature from about 0° C. to about 25° C.

Alternatively, 3-(3-amino-1H-pyrazol-1-yl)pyridine (8a) may be prepared by the coupling of 3-bromopyridine and 3-aminopyrazole in a water-miscible polar aprotic organic solvent at a temperature of about 75° C. to about 155° C. in the presence of a catalytic amount of copper chloride and a base. While stoichiometric amounts of 3-bromopyridine and 3-aminopyrazole are required, it is often convenient to use an excess of 3-aminopyrazole. An excess from about 10 mole percent to about 50 mole percent 3-aminopyrazole is preferred. The coupling is run in the presence of about 5 mole percent to about 50 mole percent copper chloride, preferably from about 15 mole percent to about 30 mole percent copper chloride. The copper chloride may be either copper (I) chloride or copper (II) chloride. The coupling is also run in the presence of a base. While stoichiometric amounts of 3-bromopyridine and base are required, it is often convenient to use about a 1.5 fold to about a 2 fold excess of base. Alkali metal carbonates are preferred bases. The coupling is performed in a water-miscible polar aprotic organic solvent. Polar aprotic organic solvents that are soluble in water include nitriles such as acetonitrile, sulfoxides such as dimethyl sulfoxide, and amides such as N-methylpyrrolidinone, N,N-dimethylformamide and N,N-dimethylacetamide. N,N-Dimethylformamide is particularly preferred.

3-(3-Amino-1H-pyrazol-1-yl)pyridine (8a) may also be prepared through a two-step reaction sequence as disclosed in Scheme 8. In step a4, 3-hydrazinopyridine dihydrochloride is treated with acrylonitrile in a $C_1$-$C_4$ aliphatic alcohol at a temperature of about 25° C. to about 100° C. in the presence of an alkali metal $C_1$-$C_4$ alkoxide to provide 1-(pyridin-3-yl)-4,5-dihydro-1H-pyrazol-3-amine (9a). While stoichiometric amounts of 3-hydrazinopyridine dihydrochloride and acrylonitrile are required, it is often convenient to use about a 1.5 fold to about a 2 fold excess of acrylonitrile. The cyclization is run in the presence of an alkali metal $C_1$-$C_4$ alkoxide base. It is often convenient to use about a 2 fold to about a 5 fold excess of base. The cyclization is performed in a $C_1$-$C_4$ aliphatic alcohol. It is most convenient that the alkoxide base and the alcohol solvent be the same, for example, sodium ethoxide in ethanol. In step b4, 1-(pyridin-3-yl)-4,5-dihydro-1H-pyrazol-3-amine (9a) is treated with an oxidant in an organic solvent at a temperature of about 25° C. to about 100° C. to provide 3-(3-amino-1H-pyrazol-1-yl)pyridine (8a). Suitable oxidants include manganese (IV) oxide, potassium ferricyanide (III), copper (I) chloride in the presence of oxygen, and iron (III) chloride in the presence of oxygen. Manganese (IV) oxide is preferred. It is often convenient to use about a 1.5 fold to about a 10 fold excess of oxidant. The oxidation is performed in a solvent that is inert to the oxidant. Suitable solvents include nitriles such as acetonitrile or halocarbons such as dichloromethane or chlorobenzene. With manganese (IV) oxide as the oxidant, acetonitrile is a preferred solvent.

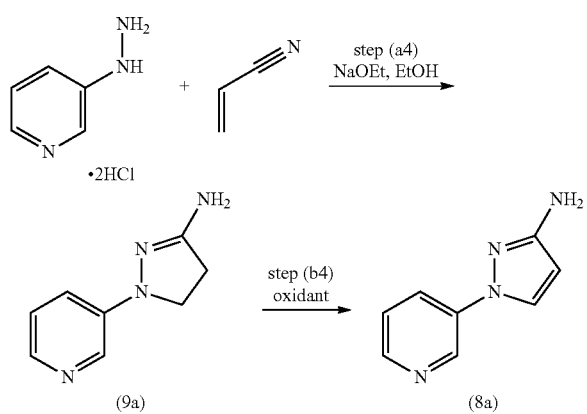

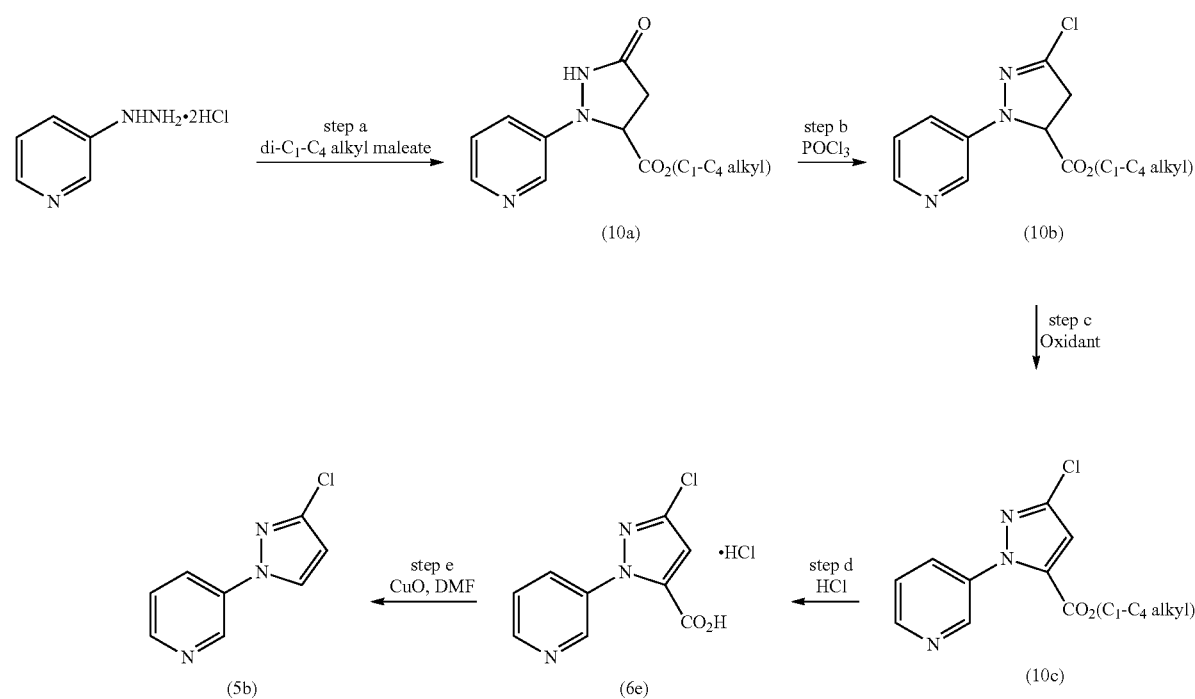

In step a of Scheme 9, 3-hydrazinopyridine.dihydrochloride is treated with a di-$C_1$-$C_4$ alkyl maleate such as diethyl maleate in a $C_1$-$C_4$ aliphatic alcohol at a temperature of about 25° C. to about 100° C. in the presence of an alkali metal $C_1$-$C_4$ alkoxide to provide pyrazolidine carboxylate (10a). While stoichiometric amounts of 3-hydrazinopyridine.dihydrochloride and di-$C_1$-$C_4$ alkyl maleate are required, it is often convenient to use about a 1.5 fold to about a 2 fold excess of di-$C_1$-$C_4$ alkyl maleate. The cyclization is run in the presence of an alkali metal $C_1$-$C_4$ alkoxide base such as sodium ethoxide. It is often convenient to use about a 2 fold to about a 5 fold excess of base. The cyclization is performed in a $C_1$-$C_4$ aliphatic alcohol such as ethanol. It is most convenient that the alkoxide base and the alcohol solvent be the same, for example, sodium ethoxide in ethanol.

In step b of Scheme 9, the pyrazolidine carboxylate (10a) may be treated with a chlorinating reagent in an inert organic solvent at a temperature of about 25° C. to about 100° C. to provide chlorinated dihydropyrazole carboxylate (10b). Suitable chlorinating reagents include phosphoryl trichloride and phosphorus pentachloride. Phosphoryl chloride is preferred. It is often convenient to use about a 1.1 fold to about a 10 fold excess of the chlorinating reagent. The chlorination is performed in an organic solvent that is inert to the chlorinating reagent. Suitable solvents include nitriles such as acetonitrile. With phosphoryl trichloride as the chlorinating reagent, acetonitrile is a preferred solvent.

In step c of Scheme 9, chlorinated dihydropyrazole carboxylate (10b) may treated with an oxidant in an organic solvent at a temperature of about 25° C. to about 100° C. to provide chlorinated pyrazole carboxylate (10c). Suitable oxidants include manganese (IV) oxide and sodium persulfate/sulfuric acid. It is often convenient to use about a 1.5 fold to about a 15 fold excess of oxidant. The oxidation is performed in an organic solvent that is inert to the oxidant. Suitable solvents include nitriles such as acetonitrile. With manganese (IV) oxide ($MnO_2$) or sodium persulfate/sulfuric acid as the oxidant, acetonitrile is a preferred solvent.

In step d of Scheme 9, chlorinated pyrazole carboxylate (10c) may then be converted to the desired 3-chloro-1-(pyridin-3-yl)-1H-pyrazole-5-carboxylic acid hydrochloride (6e) by treatment in aqueous hydrochloric acid at a temperature of about 25° C. to about 100° C. While stoichiometric amounts of reagents are required, it is often convenient to use an excess of reagents with respect to the chlorinated pyrazole carboxylate. Thus, aqueous hydrochloric acid is used in large excess as the reaction medium. Alternatively, chlorinated pyrazole carboxylates may be saponified in the presence of an inorganic base, preferably metal hydroxides or their hydrates such as lithium hydroxide hydrate ($LiOH.H_2O$) in water and a polar solvent such as dioxane at temperatures from about 0° C. to about 30° C. to yield 3-chloro-1-(pyridin-3-yl)-1H-pyrazole-5-carboxylic acid (6e).

In step e of Scheme 9, 3-chloro-1-(pyridin-3-yl)-1H-pyrazole-5-carboxylic acid hydrochloride (6e) is decarboxylated in the presence of copper (II) oxide in polar solvents such as N,N-dimethylformamide at temperatures from about 80° C. to about 140° C. to yield 3-(3-chloro-1H-pyrazol-1-yl)pyridine (5b). It was surprisingly discovered that this decarboxylation only occurs in the presence of copper (II) oxide. Several known decarboxylation agents from the literature such as, for example, hydrochloric acid (See alternate synthetic route, Example 17), sulfuric acid, and palladium (II) trifluoroacetate/trifluoroacetic acid (See "CE-7") did not yield the desired product.

EXAMPLES

The following examples are presented to better illustrate the processes of the present application.

Example 1

3-(3-Chloro-4,5-dihydro-1H-pyrazol-1-yl)pyridine (5a)

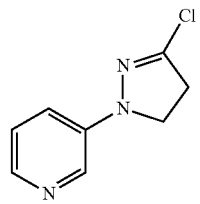 [SMILES: ClC1=NN(c2cccnc2)CC1]

A 500 mL, 3-neck round bottom flask was charged with methyl acrylate (18.9 g, 220 mmol) and ethanol (110 mL). 3-hydrazinopyridine dihydrochloride (20.0 g, 110 mmol) was added, followed by sodium ethoxide (29.9 g, 439 mmol) and the reaction was stirred at 60° C. for 6 hours, at which point thin layer chromatography (TLC) analysis [Eluent: 10% methanol/dichloromethane] indicated that the starting material had disappeared and a major product had formed: ESIMS m/z 164 ([M+H]$^+$). The reaction was allowed to cool to 20° C. and concentrated to afford a yellow solid. The resulting solid was charged with phosphoryl chloride (100 g, 654 mmol). The reaction was stirred at 60° C. for 3 hours, at which point a sample of the reaction mixture was diluted with water and basified with 15 wt % sodium hydroxide (NaOH) solution. The resulting solution was extracted with ethyl acetate (EtOAc) and the organic layer was analyzed by thin layer chromatography [Eluent: ethyl acetate], which indicated that the reaction was complete.

The reaction mixture was slowly quenched into water (400 mL) at <30° C. and the resulting solution was basified with 50 wt % sodium hydroxide solution to pH>10. The resulting solution was extracted with ethyl acetate (3×200 mL) and the organic layers were combined and concentrated to dryness. The residue was purified by flash column chromatography using 50-80% ethyl acetate/hexanes as eluent. The fractions containing pure product were concentrated to dryness and the resulting yellow solid was dried under vacuum to afford the desired product as a yellow solid (11.3 g, 66%): mp 66-68° C.; $^1$H NMR (400 MHz, DMSO-d$_6$) δ 8.28 (d, J=2.8 Hz, 1H), 8.07 (dd, J=4.5, 1.5 Hz, 1H), 7.32 (ddd, J=8.4, 2.9, 1.6 Hz, 1H), 7.26 (dd, J=8.4, 4.5 Hz, 1H), 3.93 (t, J=10.2 Hz, 2H), 3.23 (t, J=10.2 Hz, 2H); $^{13}$C NMR (101 MHz, DMSO-$d_6$) δ 144.37, 142.05, 140.50, 134.64, 123.65, 119.31, 49.63, 36.90; EIMS m/z 181 ([M]$^+$).

Example 2

3-(3-Chloro-1H-pyrazol-1-yl)pyridine (5b)

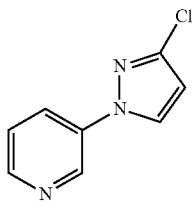 [SMILES: Clc1ccn(-c2cccnc2)n1]

A 100 mL, 3-neck round bottom flask was charged with 3-(3-chloro-4,5-dihydro-1H-pyrazol-1-yl)pyridine (3.0 g) and N,N-dimethylformamide (15 mL). potassium persulfate (6.70 g, 24.8 mmol) was added and the reaction was heated to 80° C. for 3 hours. An exotherm at about 110° C. was observed. It was allowed to cool to 80° C. and stirred at 80° C. for 3 hours, at which point a sample was diluted with water and basified with 50 wt % sodium hydroxide solution and extracted with ethyl acetate. The organic layer was analyzed by thin layer chromatography [Eluent: ethyl acetate], which showed that the desired product was formed as the major product, along with a trace of starting material and some minor impurities. The reaction mixture was cooled to 20° C. and diluted with water (50 mL). It was basified with 50% sodium hydroxide and extracted with ethyl acetate (4×30 mL). The organic layers were combined, concentrated to dryness, and purified by flash column chromatography using 30% ethyl acetate/hexanes as eluent. The pure fractions were concentrated to dryness to afford a white solid (1.60 g, 54%): mp 104-106° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (M, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

Alternate Synthetic Route to:
3-(3-Chloro-1H-pyrazol-1-yl)pyridine (5b)

Crude 3-(3-chloro-4,5-dihydro-1H-pyrazol-1-yl)pyridine (54.1 g, 232 mmol, 77.8% purity) was introduced into a 3 L three-neck round bottom flask. Water (530 mL) was then added. The mixture was heated to 60° C. and a potassium hydroxide solution (165 g, 2940 mmol) in water (500 mL) was added. The dark brown mixture was heated to 90° C. A potassium ferricyanide solution (253 g, 768 mmol) in water (700 mL) was added slowly over 30 minutes leading to brown-red mixture. The mixture was stirred at 90° C. for another 1.5 hours. The reaction mixture was cooled to below 45° C. and filtered. The filter cake was washed with water (300 mL) affording crude product as a brown solid. The crude product was then dissolved in acetonitrile (400 mL) and filtered. The organic filtrate was dried and concentrated to afford the title product as a brown solid (28.8 g, 69%, 94% purity).

Alternate Synthetic Route to:
3-(3-Chloro-1H-pyrazol-1-yl)pyridine (5b)

3-(3-Chloro-4,5-dihydro-1H-pyrazol-1-yl)pyridine (362 mg, 2.0 mol) was introduced into a 25 mL vial. Potassium hydroxide solution (658 mg, 85% pure) in water (H$_2$O) (4.0 mL) was added and the mixture was heated to 60° C. Potassium ferricyanide solution (656 mg in 1.0 mL water) was added over 15 minutes leading to brown mixture. The mixture was stirred at 62° C. for another 15 minutes. Potassium persulfate solution (270 mg, 1.0 mmol, 0.5 eq.) in water (1.0 mL) was added in one portion. The mixture was stirred at 60° C. and monitored by LC. Additional two portions of potassium persulfate solution (270 mg, 1.0 mmol, 0.5 eq.) in water (1.0 mL) was added at 1.5 hours and at 2.5 hours. The reaction mixture was stirred for a total 4.5 hours and LC indicated 88.0% conversion. The mixture was then stirred at 75° C. for 1.5 hours and LC indicated >90% conversion. After filtration, the filter cake was washed with water (10 mL) affording crude product as a pale brown solid. The crude product was then washed with acetonitrile (2×15 mL). The organic filtrate was dried and concentrated to afford desired product as light brown solid (328 mg, 91.6%, 94.0% pure by LC).

Alternate Synthetic Route to:
3-(3-Chloro-1H-pyrazol-1-yl)pyridine (5b)

To a solution of 3-(3-chloro-4,5-dihydro-1H-pyrazol-1-yl)pyridine (1.09 g, 6.00 mmol) in dry N,N-dimethylformamide (6.0 mL) in a 25 mL round bottom flask was added copper(I) chloride (0.178 g, 1.80 mmol) leading to a green suspension. Dried air was bubbled through the mixture. The resultant dark green mixture was stirred at 85° C. for 16 hours. The mixture was then cooled down and dispersed into water (20 mL) and ethyl acetate (20 mL). The mixture was filtered through a pad of Celite® and washed thoroughly with ethyl acetate (4×20 mL). Aqueous layer was extracted with ethyl acetate (4×20 mL). The combined organic extracts were dried over anhydrous sodium sulfate (Na$_2$SO$_4$) and concentrated to afford crude product (0.582 g, 51%).

Alternate Synthetic Route to:
3-(3-Chloro-1H-pyrazol-1-yl)pyridine (5b)

To a solution of 3-chloro-4,5-dihydro-1-(3-pyridinyl)-1H-pyrazole (1.82 g, 10.0 mmol) in acetonitrile (20 mL) was added manganese (IV) oxide (4.35 g, 50 mmol) (Aldrich activated). The mixture was heated at 55° C. for 10 hours. The mixture was filtered hot through Celite®, and washed with acetonitrile (2×5 mL). The light amber liquid was concentrated to give a light pink solid (1.99 g). This solid was dried at 55° C. with a nitrogen purge to give a solid (1.92 g, 83%, LC internal standard analysis indicated a purity of 77.6 wt %). A portion of the solid (1.26 g) was dissolved in hot 10% water in ethanol (6 mL). The solution was filtered hot through a sintered glass funnel to remove cloudiness. This solution was scratched and cooled overnight in a refrigerator. The solid was filtered and dried at 55° C. with a nitrogen purge to give the title compound as an off-white solid (0.512 g, mp 102× 104° C.).

Alternate Synthetic Route to:
3-(3-Chloro-1H-pyrazol-1-yl)pyridine (5b)

To a solution of 3-chloro-4,5-dihydro-1-(3-pyridinyl)-1H-pyrazole (0.182 g, 1.00 mmol) in tert-amyl alcohol (2 mL) was added manganese (IV) oxide (0.870 g, 10 mmol) (Carus black). The mixture was heated at 80° C. for 19 hours. LC analysis indicated complete conversion to product. The reaction was not worked up.

Alternate Synthetic Route to: 3-(3-Chloro-1H-pyrazol-1-yl)pyridine (5b)

To a three-neck round bottomed flask (25 mL) was introduced 3-(3-amino-1H-pyrazol-1-yl)pyridine (0.480 g, 3.00 mmol) and concentrated hydrochloric acid (4.6 mL). The vigorously stirred mixture was cooled to −5° C. using sodium chloride (NaCl) ice-bath. Sodium nitrite (0.269 g, 3.90 mmol) in water (1.3 mL) was added dropwise over 40 minutes while maintaining the temperature at −5° C. The resultant dark orange mixture was stirred for 1 hour between −5° C. and ~0° C. and then added dropwise into a suspension of copper(I) chloride (0.475 g, 4.80 mmol) in chloroform (CHCl$_3$, 4.8 mL) at 25° C. over 15 minutes. The dark green slurry was stirred at room temperature for 1 hour. Water (10 mL) and chloroform (10 mL) was added to the mixture leading to a dark green solution. The acidic aqueous solution was neutralized by sodium hydroxide (50% in water) to pH 8 and extracted with chloroform (2×10 mL) and ethyl acetate (3×20 mL). The combined organic extracts were dried over anhydrous sodium sulfate and concentrated under reduced pressure to afford crude product as a yellow solid (0.476 g). LC assay using di-n-propyl phthalate as internal standard indicated 73.7% purity (0.351 g, 65%): $^1$H NMR (400 MHz, CDCl$_3$) δ 8.94 (d, J=2.8 Hz, 1H), 8.57 (dd, J=4.8, 1.2 Hz, 1H), 8.03 (ddd, J=8.4, 2.8, 1.6 Hz, 1H), 7.90 (d, J=2.4 Hz, 1H), 7.41 (ddd, J=8.4, 4.8, 0.8 Hz, 1H), 6.45 (d, J=2.4 Hz, 1H); EIMS m/z 179 ([M]$^+$); HPLC (Zorbax SB-C8 column, P/N: 863954-306; mobile phase: A=water (0.1% formic acid), B=acetonitrile (0.01% formic acid); Gradient from 5 to 100% acetonitrile over 15 minutes; flow: 1.0 mL/minute): $t_R$=6.28 minutes.

Example 2a

3-(3-Chloro-1H-pyrazol-1-yl)pyridine (5b) hydrochloride

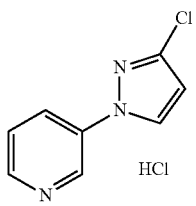

A mixture of 3-chloro-4,5-dihydro-1-(3-pyridinyl)-1H-pyrazole (0.182 g, 1.00 mmol) and manganese (IV) oxide (0.870 g, 10.0 mmol) (Carus black) in chlorobenzene (2 mL) was heated at 80° C. for 24 hours. The mixture was allowed to cool to room temperature, filtered through Celite®, and the wetcake was rinsed with chlorobenzene (2 mL). The lightly tinted solution was acidified with hydrochloric acid (4 M in 1,4-dioxane) to ~pH 1.5 to give a thick, white mixture. After stirring in an ice-bath for 30 minutes, the mixture was filtered through a sintered glass funnel and rinsed with cold chlorobenzene (2 mL). The solids (0.380 g) were allowed to air-dry in a hood overnight to give the title compound as an off-white solid (0.140 g, 64%, LC internal standard analysis indicated a purity of 98.7 wt %): mp 229-237° C.; $^1$H NMR (DMSO-d$_6$) δ 11.11 (bs, 1H), 9.27 (d, J=2.4 Hz, 1H), 8.82 (d, J=2.7 Hz, 1H), 8.71 (dd, J=5.1, 1.2 Hz, 1H), 8.61 (ddd, J=8.5, 2.5, 1.2 Hz, 1H), 7.89 (dd, J=8.5, 5.1 Hz, 1H), 6.79 (d, J=2.7 Hz, 1H).

Alternate Synthetic Route to: 3-(3-Chloro-1H-pyrazol-1-yl)pyridine (5b) hydrochloride

Step 1. 1-(Pyridin-3-yl)pyrazolidin-3-one

In a four-neck round bottomed flask (250 mL) which contained 3-hydrazinopyridine dihydrochloride (18.2 g, 0.100 mol) was added sodium ethoxide (21 wt % in ethanol, 107 g, 0.330 mol). The temperature of the slurry rose to 33° C. over 5 minutes. The mixture was stirred at room temperature for 1.25 hours. To the light red tinted slurry was added methyl acrylate (18.0 mL, 0.200 mol) over 10 minutes, with the temperature rising from 25° C. to 35° C. The color of the slurry changed from light red to brown/green. The mixture was heated at 55° C. for 3 hours. After stirring at room temperature overnight, the mixture was neutralized to pH~7 with hydrochloric acid (4 M in 1,4-dioxane, 32.6 g, 0.130 mol). The dark gray slurry was concentrated to a dark, paste like solid.

Step 2. 3-(3-chloro-4,5-dihydro-1H-pyrazol-1-yl)pyridine (5a)

To the paste-like solid obtained from Step 1 in a 4-neck round bottomed flask (500 mL) was added chlorobenzene (120 mL). Phosphoryl chloride (10.2 mL, 0.110 mol) was added dropwise to the thick mixture over 10 minutes. The temperature of the mixture went from 22° C. to 27° C. The slurry was heated at 80° C. for 1 hour. The mixture was cooled to 25° C., water (120 mL) was added to dissolve the solids, and the temperature rose to 28° C. The two phase mixture was brought to pH~12 with sodium hydroxide (50% in water, 42.8 g) using an ice-bath cooling to keep the temperature below 40° C. After cooling to 30° C., the mixture was transferred to a separatory funnel. The phases separated rapidly, and the bottom aqueous layer (containing some suspended solids) was removed from the dark organic phase. Attempted re-extraction of the aqueous phase with chlorobenzene (30 mL) resulted in an emulsion with solids present. The mixture was filtered through Celite®, the phases allowed to settle, and the organics added to the above organic phase to give a solution of the title compound as a dark amber liquid containing a small amount of fine solids (319 g, LC internal standard analysis indicated 4.3 wt % (75.4 mmol) 3-chloro-4,5-dihydro-1-(3-pyridinyl)-1H-pyrazole in the solution, for an in-pot yield of 75% starting from 3-hydrazinopyridine).

Step 3 3-(3-Chloro-1H-pyrazol-1-yl)pyridine (5b) hydrochloride

To the above solution in a round bottomed flask (500 mL) was added manganese (IV) oxide (70.0 g, 0.800 mol) and the mixture heated at 80° C. for 17 hours. The temperature was increased to 100° C. and heated for another 18 hours. The mixture was allowed to cool to 50° C. and filtered through Celite®. The amber solution was acidified with hydrochloric acid (4 M in 1,4-dioxane, 21.5 g) to pH~1.5. The thick fine precipitate was stirred at room temperature for 0.5 hours, filtered (slow, cracking of cake), and rinsed with chlorobenzene. The paste-like solid (48.99 g) was air dried in a hood overnight, the hard solid crushed with a spatula, and further dried at 55° C. with a nitrogen purge to give the title compound as a light tan solid (15.2 g, LC internal standard analysis indicated a purity of 91.9 wt %, for a 64.7% isolated yield of 3-(3-chloro-1H-pyrazol-1-yl)-pyridine hydrochloride starting from 3-hydrazinopyridine dihydrochloride).

Example 3

3-(3-Chloro-4-nitro-1H-pyrazol-1-yl)pyridine (5c)

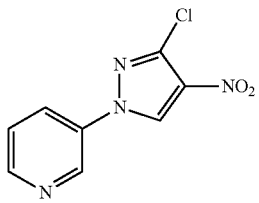 [SMILES: O=[N+]([O-])c1cn(-c2cccnc2)nc1Cl]

To a 100 mL, round bottom flask was charged 3-(3-chloro-1H-pyrazol-1-yl)pyridine (2.00 g, 11.1 mmol) and concentrated sulfuric acid (4 mL). This suspension was cooled to 5° C. and 2:1 concentrated nitric acid/sulfuric acid (3 mL, prepared by adding the concentrated sulfuric acid to a stirring and cooling solution of the nitric acid) was added dropwise at a rate such that the internal temperature was maintained <15° C. The reaction was allowed to warm to 20° C. and stirred for 18 hours. A sample of the reaction mixture was carefully diluted into water, basified with 50 wt % sodium hydroxide and extracted with ethyl acetate. Analysis of the organic layer indicated that the reaction was essentially complete. The reaction mixture was carefully added to ice cold water (100 mL) at <20° C. It was basified with 50% sodium hydroxide at <20° C. The resulting light yellow suspension was stirred for 2 hours and filtered. The filter cake was rinsed with water (3×20 mL) and dried to afford an off-white solid (2.5 g, quantitative): mp 141-143° C.; $^1$H NMR (400 MHz, DMSO-$d_6$) δ 9.86 (s, 1H), 9.23-9.06 (m, 1H), 8.75-8.60 (m, 1H), 8.33 (ddd, J=8.4, 2.8, 1.4 Hz, 1H), 7.64 (ddd, J=8.5, 4.7, 0.7 Hz, 1H); $^{13}$C NMR (101 MHz, DMSO-$d_6$) δ 149.49, 140.75, 136.02, 134.43, 132.14, 131.76, 127.22, 124.31; EIMS m/z 224 ([M]$^+$).

Example 4

3-(3-Chloro-4-amino-1H-pyrazol-1-yl)pyridine (5d)

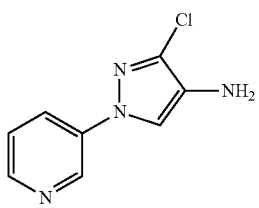 [SMILES: Nc1cn(-c2cccnc2)nc1Cl]

To a 100 mL, 3-neck round bottom flask was charged 3-(3-chloro-4-nitro-1H-pyrazol-1-yl)pyridine (2.40 g, 10.7 mmol), acetic acid (4 mL), ethanol (4.8 mL) and water (4.8 mL). The mixture was cooled to 5° C. and iron powder (2.98 g, 53.4 mmol) was added portionwise over ~15 minutes. The reaction was allowed to stir at 20° C. for 18 hours and diluted to 50 mL with water. It was filtered through Celite® and the filtrate was carefully basified with 50 wt % sodium hydroxide solution. The resulting suspension was filtered through Celite® and the filtrate was extracted with ethyl acetate (3×20 mL). The organic layers were combined and dried over sodium sulfate and concentrated to dryness to afford a tan colored solid, which was further dried under vacuum for 18 hours (2.20 g, quantitative): mp 145-147° C.; $^1$H NMR (400 MHz, DMSO-$d_6$) δ 8.95 (dd, J=2.6, 0.8 Hz, 1H), 8.45 (dd, J=4.7, 1.4 Hz, 1H), 8.08 (ddd, J=8.4, 2.7, 1.4 Hz, 1H), 7.91 (s, 1H), 7.49 (ddd, J=8.3, 4.7, 0.8 Hz, 1H), 4.43 (s, 2H); $^{13}$C NMR (101 MHz, DMSO-$d_6$) δ 146.35, 138.53, 135.72, 132.09, 130.09, 124.29, 124.11, 114.09; EIMS m/z 194 ([M]$^+$).

Alternate Synthetic Route to: 3-(3-Chloro-4-amino-1H-pyrazol-1-yl)pyridine (5d)

In a 250 mL 3-neck round bottom flask was added 3-(3-chloro-4-nitro-1H-pyrazol-1-yl)pyridine (5.00 g, 21.8 mmol), ethanol (80 mL), water (40 mL), and ammonium chloride (5.84 g, 109 mmol). The suspension was stirred under nitrogen stream for 5 minutes then iron powder (4.87 g, 87.2 mmol) added. The reaction mixture was heated to reflux (~80° C.) and held there for 4 hours. After 4 hours a reaction aliquot taken showed by HPLC analysis the reaction had gone to full conversion. Ethyl acetate (120 mL) and Celite® (10 g) were added to the reaction mixture and let stir for 10 minutes. The black colored suspension was then filtered via a Celite® pad and the pad rinsed with ethyl acetate (80 mL). The reaction mixture was washed with saturated sodium bicarbonate (30 mL) and the organic layer was assayed. The assay gave (4.19 g, 99%) of product. The organic solvent was removed in vacuo to give a brown colored crude solid that was used without further purification.

Example 5

N-(3-Chloro-1-(pyridin-3-yl)-1H-pyrazol-4-yl)-3-((3,3,3-trifluoropropyl)thio)propanamide (Compound 5.5)

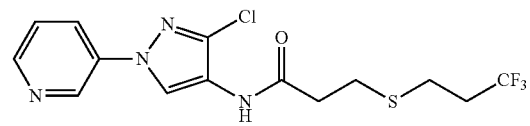 [SMILES: O=C(CCSCCC(F)(F)F)Nc1cn(-c2cccnc2)nc1Cl]

A 100-mL, three-neck round bottom flask was charged with 3-chloro-(pyridin-3-yl)-1H-pyrazol-4-amine (1.00 g, 5.14 mmol) and ethyl acetate (10 mL). Sodium bicarbonate (1.08 g, 12.9 mmol) was added, followed by dropwise addition of 3-((3,3,3-trifluoropropyl)thio)propanoyl chloride (1.36 g, 6.17 mmol) at <20° C. The reaction was stirred at 20° C. for 2 hours, at which point thin layer chromatography analysis [Eluent: ethyl acetate] indicated that the reaction was complete. The reaction was diluted with water (50 mL) and the layers separated. The aqueous layer was extracted with ethyl acetate (20 mL) and the combined organic layers were concentrated to dryness to afford a light brown oil. The residue was purified by flash column chromatography using 30-60% ethyl acetate/hexanes. The fractions containing pure product were concentrated to dryness to afford a white solid (1.40 g, 72%): mp 99-102° C.; $^1$H NMR (400 MHz, DMSO-$d_6$) δ 9.92 (s, 1H), 9.05 (d, J=2.7 Hz, 1H), 8.86 (s, 1H), 8.54 (dd, J=4.5, 1.4 Hz, 1H), 8.21 (ddd, J=8.4, 2.7, 1.4 Hz, 1H), 7.54 (dd, J=8.4, 4.7 Hz, 1H), 2.86 (t, J=7.3 Hz, 2H), 2.74 (td, J=6.5, 5.6, 4.2 Hz, 4H), 2.59 (ddd, J=11.7, 9.7, 7.4 Hz, 2H); $^{13}$C NMR (101 MHz, DMSO-$d_6$) δ 169.32, 147.49, 139.44, 135.47, 133.40, 126.60 (q, J=296 Hz), 125.49, 124.23, 122.30, 120.00, 35.18, 33.42 (q, J=27.2 Hz), 26.77, 23.05 (q, J=3.3 Hz); EIMS m/z 378 ([M]+).

Example 6

3-((3,3,3-Trifluoropropyl)thio)propanoic acid

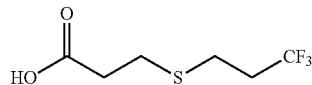 [SMILES: O=C(O)CCSCCC(F)(F)F]

A 100 mL, 3-neck round bottom flask was charged with 3-bromopropanoic acid (500 mg, 3.27 mmol) and methanol (10 mL), potassium hydroxide (403 mg, 7.19 mmol) was added, followed by 3,3,3-trifluoropropane-1-thiol (468 mg, 3.60 mmol). The mixture was heated at 50° C. for 4 hours, after which it was acidified with 2 N hydrochloric acid and extracted with methyl tert-butylether (MTBE, 2×10 mL). The organic layer was concentrated to dryness to afford a light yellow oil (580 mg, 88%): $^1$H NMR (400 MHz, CDCl$_3$) δ 2.83 (td, J=7.1, 0.9 Hz, 2H), 2.78-2.64 (m, 4H), 2.48-2.32 (m, 2H).

Alternate Synthetic Route to:
3-((3,3,3-Trifluoropropyl)thio)propanoic acid

A 100 mL stainless steel Parr reactor was charged with azobisisobutyronitrile (AIBN, 0.231 g, 1.41 mmol), toluene (45 mL), 3-mercaptopropionic acid (3.40 g, 32.0 mmol), and octanophenone (526.2 mg) as an internal standard, and was purged and pressure checked with nitrogen (N$_2$). The reactor was cooled with dry ice and the 3,3,3-trifluoropropene (3.1 g, 32.3 mmol) was condensed into the reactor. The ice bath was removed and the reactor heated to 60° C. and stirred for 27 hours. The internal yield of the reaction was determined to be 80% by use of the octanophenone internal standard. The pressure was released and the crude mixture removed from the reactor. The mixture was concentrated by rotary evaporation and 50 mL of 10% sodium hydroxide was added. The solution was washed with methyl tert-butylether (50 mL) then acidified to pH~1 with 6 N hydrochloric acid. The product was extracted with 100 mL methyl tert-butylether, dried over magnesium sulfate (MgSO$_4$), filtered, and concentrated to give the crude titled compound as an oil (5.34 g, 26.4 mmol, 83%): $^1$H NMR (400 MHz, CDCl$_3$) δ 2.83 (td, J=7.1, 0.9 Hz, 2H), 2.76-2.64 (m, 4H), 2.47-2.30 (m, 2H); $^{13}$C NMR (101 MHz, CDCl$_3$) δ 177.68, 125.91 (q, J=277.1 Hz), 34.58 (q, J=28.8 Hz), 34.39, 26.63, 24.09 (q, J=3.3 Hz); $^{19}$F NMR (376 MHz, CDCl$_3$) δ −66.49.

Alternate Synthetic Route to:
3-((3,3,3-Trifluoropropyl)thio)propanoic acid

A 250 mL three-neck round bottomed flask was charged with toluene (81 mL) and cooled to <−50° C. with a dry ice/acetone bath. 3,3,3-Trifluoropropene (10.28 g, 107.0 mmol) was bubbled into the solvent and the ice bath was removed. 3-Mercaptopropionic acid (9.200 g, 86.70 mmol) and 2,2-dimethoxy-2-phenylacetophenone (1.070 g, 4.170 mmol) was added and the long wave light (366 nm, 4 watt UVP lamp) was turned on (Starting temperature: −24° C.). The reaction reached a temperature of 27.5° C. due to heat from the lamp. The reaction was stirred with the black light on for 4 hours. After 4 hours the black light was turned off and the reaction concentrated by rotary evaporation (41° C., 6 mm Hg) giving a pale yellow oil (18.09 g, 51:1 linear:branched isomer, 90 wt % linear isomer by GC internal standard assay, 16.26 g active, 93%). The crude material was dissolved in 10% sodium hydroxide w/w (37.35 g) and was washed with toluene (30 mL) to remove non-polar impurities. The aqueous layer was acidified to pH~2-3 with hydrochloric acid (2 N, 47.81 g) and was extracted with toluene (50 mL). The organic layer was washed with water (40 mL) and dried over magnesium sulfate, filtered, and concentrated by rotary evaporation giving a pale yellow oil (14.15 g, 34:1 linear:branched isomer, 94 wt % linear isomer by GC internal standard assay, 13.26 g active, 76%).

Alternate Synthetic Route to:
3-((3,3,3-Trifluoropropyl)thio)propanoic acid

A 100 mL stainless steel Parr reactor was charged with 3-mercaptopropionic acid (3.67 g, 34.6 mmol), toluene (30.26 g), and 2,2'-azobis(4-methoxy-2,4-dimethyl) valeronitrile (V-70, 0.543 g, 1.76 mmol) and the reactor was cooled with a dry ice/acetone bath, purged with nitrogen, and pressure checked. 3,3,3-Trifluoropropene (3.20 g, 33.3 mmol) was added via transfer cylinder and the reaction was allowed to warm to 20° C. After 24 hours, the reaction was heated to 50° C. for 1 hour to decompose any remaining V-70 initiator. The reaction was allowed to cool to room temperature. The solution was concentrated by rotary evaporation to provide the title compound (6.80 g, 77.5 wt % linear isomer by GC internal standard assay, 5.27 g active, 76%, 200:1 linear:branched by GC, 40:1 linear:branched by fluorine NMR).

Example 7

Methyl-3-((3,3,3-trifluoropropyl)thio)propionate

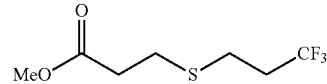 [SMILES: COC(=O)CCSCCC(F)(F)F]

A 100 mL stainless steel Parr reactor was charged with azobisisobutyronitrile (0.465 g, 2.83 mmol), toluene (60 mL) and methyl-3-mercaptopropionate (7.40 g, 61.6 mmol) and was purged and pressure checked with nitrogen. The reactor was cooled with dry ice and the 3,3,3-trifluopropropene (5.7 g, 59.3 mmol) was condensed into the reactor. The ice bath was removed and the reactor heated to 60° C. and stirred to 24 hours. The heat was turned off and the reaction left at room temperature (about 22° C.) overnight. The mixture was removed from the reactor and concentrated to a yellow liquid. The liquid was distilled by vacuum distillation (2 Torr, 85° C.) and three fractions were collected: fraction 1 (1.3 g, 6.01 mmol, 10%, 70.9 area % by GC), fraction 2 (3.7 g, 17.1 mmol, 29%, 87 area % by GC), and fraction 3 (4.9 g, 22.7 mmol, 38%, 90.6 area % by GC): $^1$H NMR (400 MHz, CDCl$_3$) δ 3.71 (s, 3H), 2.82, (td, J=7.3, 0.7 Hz, 2H), 2.75-2.68 (m, 2H), 2.63 (td, J=7.2, 0.6 Hz, 2H), 2.47-2.31 (m, 2H); $^{13}$C NMR (101 MHz, CDCl$_3$) δ 172.04, 125.93 (q, J=277.2 Hz), 51.86, 34.68 (q, J=28.6 Hz), 34.39, 27.06, 24.11 (q, J=3.3 Hz); $^{19}$F NMR (376 MHz, CDCl$_3$) δ −66.53.

Alternate Synthetic Route to: Methyl-3-((3,3,3-trifluoropropyl)thio)propionate A 500 mL three-neck round bottomed flask was charged with toluene (200 mL) and cooled to <-50° C. with a dry ice/acetone bath. 3,3,3-Trifluoropropene (21.8 g, 227 mmol) was condensed into the reaction by bubbling the gas through the cooled solvent and the ice bath was removed. Methyl 3-mercaptopropionate (26.8 g, 223 mmol) and 2,2-dimethoxy-2-phenylacetophenone (2.72 g, 10.61 mmol) were added and a UVP lamp (4 watt) that was placed within 2 centimeters of the glass wall was turned on to the long wave function (366 nanometers). The reaction reached 35° C. due to heat from the lamp. After 4 hours, all of the trifluoropropene was either consumed or boiled out of the reaction. The light was turned off and the reaction stirred at room temperature overnight. After 22 hours, more trifluoropropene (3.1 g) was bubbled through the mixture at room temperature and the light was turned on for an additional 2 hours. The reaction had reached 93% conversion, so no more trifluoropropene was added. The light was turned off and the mixture concentrated on the rotovap (40° C., 20 torr) giving a yellow liquid (45.7 g, 21.3:1 linear:branched isomer, 75 wt % pure linear isomer determined by a GC internal standard assay, 34.3 g active, 71% in pot yield).

Alternate Synthetic Route to: Methyl-3-((3,3,3-trifluoropropyl)thio)propionate A 100 mL stainless steel Parr reactor was charged with methyl 3-mercaptopropionate (4.15 g, 34.5 mmol), toluene (30.3 g), and 2,2'-azobis(4-methoxy-2,4-dimethyl) valeronitrile (V-70, 0.531 g, 1.72 mmol) and the reactor was cooled with a dry ice/acetone bath, purged with nitrogen, and pressure checked. 3,3,3-Trifluoropropene (3.40 g, 35.4 mmol) was added via transfer cylinder and the reaction was allowed to warm to 20° C. After 23 hours the reaction was heated to 50° C. for 1 hour to decompose any remaining V-70 initiator. The reaction was allowed to cool to room temperature. The solution was concentrated to provide the title compound (7.01 g, 66%, 70.3 wt % linear isomer by GC internal standard assay, 4.93 g active, 66%, 24:1 linear:branched by GC, 18:1 linear:branched by fluorine NMR).

Example 8

N-(3-Chloro-1-(pyridin-3-yl)-1H-pyrazol-4-yl)-N-ethyl-3-((3,3,3-trifluoropropyl)thio)propanamide (Compound 8.5)

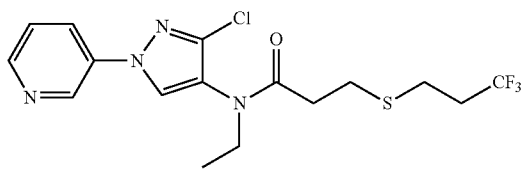 [SMILES: CCN(C(=O)CCSCCC(F)(F)F)c1cn(-c2cccnc2)nc1Cl]

A 100 mL, 3-neck round bottom flask, equipped with mechanical stirrer, temperature probe and nitrogen inlet was charged with cesium carbonate (654 mg, 2.01 mmol), N-(3-chloro-1-(pyridin-3-yl)-1H-pyrazol-4-yl)-3-((3,3,3-trifluoropropyl)thio)propanamide (380 mg, 1.00 mmol) and N,N-dimethylformamide (5 mL). Iodoethane (0.0890 mL, 1.10 mmol) was added dropwise. The reaction was stirred at 40° C. for 2 hours, at which point thin layer chromatography analysis (Eluent: ethyl acetate) indicated that only a trace of starting material remained. The reaction mixture was cooled to 20° C. and water (20 mL) was added. It was extracted with ethyl acetate (2×20 mL) and the combined organic layer was concentrated to dryness at <40° C. The residue was purified by flash column chromatography using 0-100% ethyl acetate/hexanes as eluent. The fractions containing pure product were concentrated to dryness to afford a colorless oil (270 mg, 66%): mp 79-81° C.; $^1$H NMR (400 MHz, DMSO-$d_6$) δ 9.11 (d, J=2.7 Hz, 1H), 8.97 (s, 1H), 8.60 (dd, J=4.8, 1.4 Hz, 1H), 8.24 (ddd, J=8.4, 2.8, 1.4 Hz, 1H), 7.60 (ddd, J=8.4, 4.7, 0.8 Hz, 1H), 3.62 (q, J=7.1 Hz, 2H), 2.75 (t, J=7.0 Hz, 2H), 2.66-2.57 (m 2H), 2.57-2.44 (m, 2H), 2.41 (t, J=7.0 Hz, 2H), 1.08 (t, J=7.1 Hz, 3H); EIMS m/z 406 ([M]$^+$).

Alternate Synthetic Route to: N-(3-Chloro-1-(pyridin-3-yl)-1H-pyrazol-4-yl)-N-ethyl-3-((3,3,3-trifluoropropyl)thio)propanamide (Compound 8.5)

To 3-neck round bottomed flask (50 mL) was added sodium hydride (60% in oil, 0.130 g, 3.28 mmol) and sulfolane (16 mL). The gray suspension was stirred for 5 minutes then N-(3-chloro-1-(pyridin-3-yl)-1H-pyrazol-4-yl)-3-((3,3,3-trifluoropropyl)thio)propanamide (1.20 g, 3.16 mmol) dissolved in sulfolane (25 mL) was slowly added dropwise over 5 minutes. The mixture became a light gray suspension after 3 minutes and was allowed to stir for 5 minutes after which time ethyl bromide (0.800 mL, 10.7 mmol) and potassium iodide (0.120 g, 0.720 mmol) were added sequentially. The cloudy suspension was then allowed to stir at room temperature. The reaction was quenched after 6 hours by being poured drop-wise into cooled ammonium formate/acetonitrile solution (30 mL). The resulting orange colored solution was stirred and tetrahydrofuran (40 mL) was added. The mixture was assayed, using octanophenone as a standard, and found to contain 1.09 g (85%) of the desired product with a selectivity versus the retro-Michael-like decomposition product of 97:3.

Example 9

N-(3-Chloro-1-(pyridin-3-yl)-1H-pyrazol-4-yl)-N-ethyl-3-((3,3,3-trifluoropropyl)sulfoxo)propanamide (Compound 9.5)

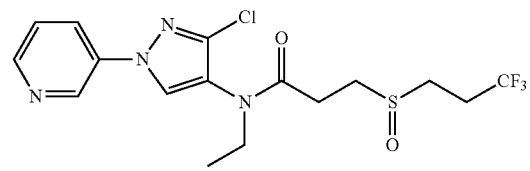 [SMILES: CCN(C(=O)CCS(=O)CCC(F)(F)F)c1cn(-c2cccnc2)nc1Cl]

N-(3-Chloro-1-(pyridin-3-yl)-1H-pyrazol-4-yl)-N-ethyl-3-((3,3,3-trifluoropropyl)thio) propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate (Na$_2$CO$_3$). The organic layer was dried over sodium sulfate and concentrated to provide a thick yellow oil. The crude product was purified by flash column chromatography using 0-10% methanol/ethyl acetate as eluent and the pure fractions were combined and concentrated to afford the desired product as an oil (42.6 g, 68%): $^1$H NMR (400 MHz, DMSO-d$_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); ESIMS m/z 423 ([M+H]$^+$).

Example 10

3-(3-Chloro-1H-pyrazol-1-yl)pyridine (5b)

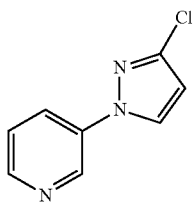

A 250 mL, 3-neck round bottom flask was charged with methyl 2-acetamidoacrylate (4.91 g, 34.3 mmol) and ethanol (40 mL). 3-Hydrazinopyridine dihydrochloride (5 g, 27.5 mmol) was added, followed by sodium ethoxide (7.48 g, 110 mmol) and the reaction was stirred at 60° C. for 6 hours, at which point thin layer chromatography analysis [Eluent: 10% methanol/dichloromethane] indicated that the starting material had disappeared and a major product had formed: ESIMS m/z 221 ([M+H]$^+$). The reaction was allowed to cool to room temperature and concentrated to afford a yellow solid. The resulting solid was slowly charged with phosphoryl chloride (29.2 g, 191 mmol). The reaction was stirred at 60° C. for 3 hours, at which point a sample of the reaction mixture was diluted with water and basified with 50 wt % sodium hydroxide solution. The resulting solution was extracted with ethyl acetate and the organic layer was analyzed by thin layer chromatography [Eluent: ethyl acetate], which indicated that the reaction was complete. The reaction mixture was concentrated at 40° C. to remove phosphoryl chloride and the residue was slowly quenched with water (40 mL) at <30° C. The resulting solution was basified with 50 wt % sodium hydroxide solution and the resulting suspension was extracted with ethyl acetate (3×50 mL). The organic layers were concentrated to dryness and the residue was purified by flash column chromatography using 40-50% ethyl acetate/hexanes. The fractions containing the pure product were concentrated to dryness to afford a white solid, which was further dried under vacuum at room temperature to afford the desired product as a white solid (2.4 g, 49%): mp 104-106° C.; $^1$H NMR (400 MHz, CDCl$_3$) δ 8.93 (d, J=27 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (m, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

Example 11

3-Chloro-N-(3-chloro-1-(pyridine-3-yl)-1H-pyrazol-4-yl)propanamide (5e)

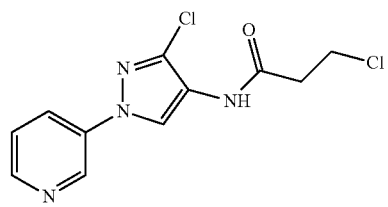 [SMILES: O=C(CCCl)Nc1cn(-c2cccnc2)nc1Cl]

A 100 mL, three-neck round bottom flask was charged with 3-chloro-1-(pyridine-3-yl)-1H-pyrazol-4-amine (1.00 g, 5.14 mmol) and ethyl acetate (10 mL). Sodium bicarbonate (1.08 g, 6.17 mmol) was added and the reaction mixture was cooled to 5° C. 3-Chloropropanoyl chloride (0.783 g, 6.17 mmol) was added dropwise at <20° C. The reaction was allowed to warm up to 20° C. and stirred for 2 hours, at which point thin layer chromatography analysis (Eluent: ethyl acetate) indicated that the reaction was complete. The reaction was diluted with water (50 mL) and the layers separated. The aqueous layer was extracted with ethyl acetate (20 mL) and the combined organic layers were concentrated to dryness to afford a white solid (1.40 g, 96%): mp 152-154° C.; $^1$H NMR (400 MHz, DMSO-d$_6$) δ 10.04 (s, 1H), 9.07 (d, J=2.7 Hz, 1H), 8.89 (s, 1H), 8.54 (dd, J=4.7, 1.4 Hz, 1H), 8.23 (ddd, J=8.4, 2.7, 1.4 Hz, 1H), 7.54 (dd, J=8.4, 4.7, Hz, 1H), 3.90 (t, J=6.2 Hz, 2H), 2.94 (t, J=6.2 Hz, 2H); $^{13}$C NMR (101 MHz, DMSO-d$_6$) δ 167.90, 147.50, 139.47, 135.46, 133.47, 125.51, 124.20, 122.47, 119.87, 40.63, 37.91; ESIMS m/z 285 ([M+H]$^+$).

Example 12

N-(3-Chloro-1-(pyridin-3-yl)-1H-pyrazol-4-yl)-3-((3,3,3-trifluoropropyl)thio)propanamide (Compound 5.5)

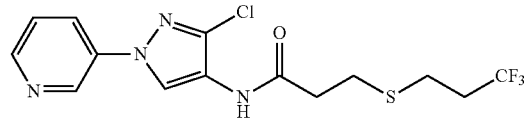 [SMILES: O=C(CCSCCC(F)(F)F)Nc1cn(-c2cccnc2)nc1Cl]

A 100 mL, 3-neck round bottom flask was charged with 3-chloro-N-(3-chloro-1-(pyridine-3-yl)-1H-pyrazol-4-yl) propanamide (570 mg, 2.00 mmol) and methanol (10 mL), potassium hydroxide (135 mg, 2.40 mmol) was added, followed by 3,3,3-trifluoropropane-1-thiol (312 mg, 2.40 mmol) The mixture was heated at 50° C. for 4 hours, at which point thin layer chromatography analysis [Eluent: ethyl acetate] indicated the reaction was complete to give exclusively a new product. It was cooled to 20° C. and diluted with water (20 mL) and ethyl acetate (20 mL). The layers were separated and the aqueous layer was extracted with ethyl acetate (20 mL). The organics were dried over sodium sulfate and concentrated to dryness to afford a light yellow oil, which solidified upon standing to give a light yellow solid (700 mg, 92%): mp 99-102° C.; ¹H NMR (400 MHz, DMSO-d₆) δ 9.92 (s, 1H), 9.05 (d, J=2.7 Hz, 1H), 8.86 (s, 1H), 8.54 (dd, J=4.5, 1.4 Hz, 1H), 8.21 (ddd, J=8.4, 2.7, 1.4 Hz, 1H), 7.54 (dd, J=8.4, 4.7 Hz, 1H), 2.86 (t, J=7.3 Hz, 2H), 2.74 (td, J=6.5, 5.6, 4.2 Hz, 4H), 2.59 (ddd, J=11.7, 9.7, 7.4 Hz, 2H); ¹³C NMR (101 MHz, DMSO-d₆) δ 169.32, 147.49, 139.44, 135.47, 133.40, 126.60 (q, J=296 Hz), 125.49, 124.23, 122.30, 120.00, 35.18, 33.42 (q, J=27.2 Hz), 26.77, 23.05 (q, J=3.3 Hz); EIMS m/z 378 ([M]⁺).

Example 13

3-((3,3,3-trifluoropropyl)thio)propanoyl chloride

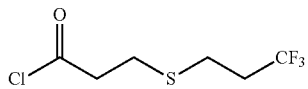 [SMILES: O=C(Cl)CCSCCC(F)(F)F]

A dry 5 L round bottom flask equipped with magnetic stirrer, nitrogen inlet, reflux condenser, and thermometer, was charged with 3-((3,3,3-trifluoropropyl)thio)propanoic acid (188 g, 883 mmol) in dichloromethane (3 L). Thionyl chloride (525 g, 321 mL, 4.42 mol) was then added dropwise over 50 minutes. The reaction mixture was heated to reflux (about 36° C.) for two hours, then cooled to room temperature. Concentration under vacuum on a rotary evaporator, followed by distillation (40 Torr, product collected from 123-127° C.) gave the title compound as a clear colorless liquid (177.3 g, 86%): ¹H NMR (400 MHz, CDCl₃) δ 3.20 (t, J=7.1 Hz, 2H), 2.86 (t, J=7.1 Hz, 2H), 2.78-2.67 (m, 2H), 2.48-2.31 (m, 2H); ¹⁹F NMR (376 MHz, CDCl₃) δ –66.42, –66.43, –66.44, –66.44.

Example 14

3-(((2,2-Difluorocyclopropyl)methyl)thio)propanoic acid

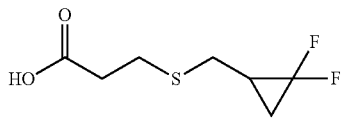 [SMILES: O=C(O)CCSCC1CC1(F)F]

Powdered potassium hydroxide (423 mg, 7.54 mmol) and 2-(bromomethyl)-1,1-difluorocyclopropane (657 mg, 3.84 mmol) were sequentially added to a stirred solution of 3-mercaptopropanoic acid (400 mg, 3.77 mmol) in methanol (2 mL) at room temperature. The resulting white suspension was stirred at 65° C. for 3 hours and quenched with 1N aqueous hydrochloric acid and diluted with ethyl acetate. The organic phase was separated and the aqueous phase extracted with ethyl acetate (2×50 mL). The combined organic extracts were dried over magnesium sulfate, filtered and concentrated in vacuo to give the title molecule as a colorless oil (652 mg, 84%): IR (KBr thin film) 3025, 2927, 2665, 2569, 1696 cm⁻¹; ¹H NMR (400 MHz, CDCl₃) δ 2.85 (t, J=7.0 Hz, 2H), 2.82-2.56 (m, 4H), 1.88-1.72 (m, 1H), 1.53 (dddd, J=12.3, 11.2, 7.8, 4.5 Hz, 1H), 1.09 (dtd, J=13.1, 7.6, 3.7 Hz, 1H); ESIMS m/z 195.1 ([M–H]⁻).

Example 15

3-(((2,2-Difluorocyclopropyl)methyl)thio)propanoyl chloride

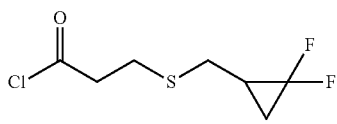 [SMILES: O=C(Cl)CCSCC1CC1(F)F]

In a 3 L 3-neck round bottomed-flask equipped with an overhead stirrer, a temperature probe, and addition funnel and an nitrogen inlet was charged with 3-(((2,2-difluorocyclopropyl)-methyl)thio)propanoic acid (90.0 g, 459 mmol) that was immediately taken up in dichloromethane (140 mL) with stirring. At room temperature, thionyl chloride (170 mL, 2293 mmol) in dichloromethane (100 mL) was added drop-wise with stirring. The reaction mixture was heated to 40° C. and heated for 2 hours. The reaction was determined to be complete by ¹H NMR (An aliquot of the reaction mixture was taken, and concentrated down via rotary evaporator). The reaction was allowed to cool to room temperature and the mixture was transferred to a dry 3 L round-bottom flask and concentrated via the rotary evaporator. This resulted in 95 g of a honey-colored oil. The contents were gravity filtered through paper and the paper rinsed with diethyl ether (10 mL). The rinse was added to the flask. This gave a clear yellow liquid. The liquid was placed on a rotary evaporator to remove the ether. This gave 92.4 g of a yellow oil. The oil was Kugelrohr distilled (bp 100-110° C./0.8-0.9 mm Hg) to provide the title compound as a colorless oil (81.4 g, 81%): ¹H NMR (400 MHz, CDCl₃) δ 3.27-3.12 (m, 2H), 2.89 (t, J=7.1 Hz, 2H), 2.67 (ddd, J=6.8, 2.6, 1.0 Hz, 2H), 1.78 (ddq, J=13.0, 11.3, 7.4 Hz, 1H), 1.64-1.46 (m, 1H), 1.09 (dtd, J=13.2, 7.7, 3.7 Hz, 1H).

Example 16

3-(3-Amino-1H-pyrazol-1-yl)pyridine (8a)

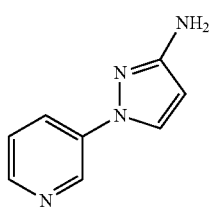 [SMILES: Nc1ccn(-c2cccnc2)n1]

To a three-neck round bottomed flask (50 mL) equipped with a reflux condenser was introduced 3-hydrazinopyridine.dihydrochloride (1.82 g, 10.0 mmol) and anhydrous ethanol (10.0 mL). Sodium ethoxide (21 wt % in ethanol, 11.8 mL, 31.5 mmol) was added over 5 minutes and the internal temperature increased from 23° C. to 30° C. The resultant light brown slurry turned light pink after stirring for 10 minutes. 3-Ethoxyacrylonitrile (2.06 mL, 20.0 mmol) was added over 5 minutes and the internal temperature remained at 30°

C. The yellow mixture was stirred at 78° C. under nitrogen for 5 hours and was then cooled to 15° C. Hydrochloric acid (4 M in 1,4-dioxane, 2.90 mL) was added slowly to quench any excess base forming a light brown suspension. The mixture was concentrated under reduced pressure to afford a brown solid. The solid was partitioned in water (30 mL) and ethyl acetate (50 mL). The insoluble light brown solid was collected by filtration to afford the first portion of product (0.340 g, >95% pure by $^1$H NMR). The aqueous layer was extracted with ethyl acetate (3×50 mL). The combined organic extracts were concentrated to afford dark brown wet solid. The mixture was suspended in ethyl acetate (10 mL), filtered, and washed with heptane (20 mL) to afford the second portion of product as a brown solid (1.00 g, >95% pure by $^1$H NMR). The title compound was obtained as a brown solid (1.34 g, 84%): $^1$H NMR (400 MHz, DMSO-$d_6$) δ 8.93 (d, J=2.4 Hz, 1H), 8.33 (dd, J=4.8, 1.2 Hz, 1H), 8.23 (d, J=2.4 Hz, 1H), 8.01 (ddd, J=8.4, 2.8, 1.2 Hz, 1H), 7.42 (dd, J=8.4, 4.8 Hz, 1H), 5.80 (d, J=2.4 Hz, 1H), 5.19 (bs, 2H, —NH$_2$); $^{13}$C NMR (100 MHz, DMSO-$d_6$) δ 157.7, 144.7, 138.0, 136.2, 128.3, 123.9, 123.2, 97.1; EIMS m/z 160 ([M]$^+$); HPLC (Zorbax SB-C8 column, P/N: 863954-306; mobile phase: A=water (0.1% formic acid), B=acetonitrile (0.01% formic acid); Gradient from 5 to 100% acetonitrile over 15 minutes; flow: 1.0 mL/minute): $t_R$=1.95 minutes.

Alternate Synthetic Route to:
3-(3-Amino-1H-pyrazol-1-yl)pyridine (8a)

A 4-neck round bottomed flask (500 mL) was charged with copper(I) chloride (2.51 g, 25.3 mmol), 1H-pyrazol-3-amine (15.8 g, 190 mmol), potassium carbonate (35.0 g, 253 mmol), and N,N-dimethylformamide (100 mL). The mixture was stirred under nitrogen for 10 minutes and 3-bromopyridine (12.2 mL, 127 mmol) was added. The mixture was heated at 110° C. for 18 hours, at which point HPLC analysis indicated that ~15.5% 3-bromopyridine remained. The reaction was allowed to cool to 20° C. and concentrated to give a brown residue. Water (200 mL) was added and the resulting suspension was stirred at 20° C. for 2 hours and filtered. The solid was rinsed with water (2×50 mL) and dried to afford a pale green solid. The solid was suspended in water (200 mL) and the resulting suspension was heated at 90° C. for 2 hours and was filtered hot through a Celite® pad. The pad was rinsed with hot water (50 mL). The combined filtrates were allowed to cool to 20° C. to afford a yellow suspension, which was stirred at 20° C. for 2 hours and filtered. The solid was rinsed with water (2×50 mL) and air dried to afford the desired product as a light yellow crystalline solid (11.6 g, 57%).

Alternate Synthetic Route to:
3-(3-amino-1H-pyrazol-1-yl)pyridine (8a)

Step 1. 1-(Pyridin-3-yl)-4,5-dihydro-1H-pyrazol-3-amine (9a)

To a 4-neck, round bottomed flask (250 mL) was charged sodium ethanolate (21 wt % in ethanol, 32 mL). 3-Hydrazinopyridine.dihydrochloride (5.00 g, 27.5 mmol) was added, causing an exotherm from 20° C. to 58° C. The mixture was allowed to cool to 20° C. and acrylonitrile (2.91 g, 54.9 mmol) was added. The reaction was heated at 60° C. for 5 hours and cooled to 20° C. The excess sodium ethanolate was quenched with hydrochloric acid (4 M in 1,4-dioxane, 6.88 mL, 27.5 mmol) at <20° C. The mixture was absorbed on silica gel (10 g) and concentrated to dryness. The crude product was purified by flash column chromatography using 0-10% methanol/dichloromethane as eluent. The fractions containing pure product were concentrated to dryness to afford the title compound as a yellow solid (3.28 g, 74%): mp 156-160° C.; $^1$H NMR (400 MHz, CDCl$_3$) δ 8.24 (dd, J=2.8, 0.8 Hz, 1H), 8.01 (dd, J=4.6, 1.4 Hz, 1H), 7.22 (ddd, J=8.4, 2.8, 1.5 Hz, 1H), 7.12 (ddd, J=8.4, 4.6, 0.8 Hz, 1H), 4.20 (s, 2H), 3.70 (t, J=9.3 Hz, 2H), 2.92 (t, J=9.3 Hz, 2H); $^{13}$C NMR (101 MHz, CDCl$_3$) δ 154.23, 144.78, 139.22, 135.08, 123.44, 119.44, 49.23, 32.74; ESIMS m/z 163 ([M+H]$^+$).

Step 2. 1-(Pyridin-3-yl)-4,5-dihydro-1H-pyrazol-3-amine (8a)

To a 3-neck, round bottomed flask (100 mL) was charged 1-(pyridin-3-yl)-4,5-dihydro-1H-pyrazol-3-amine (1.00 g, 6.17 mmol) and acetonitrile (20 mL). Manganese (IV) oxide (2.68 g, 30.8 mmol) was added, causing an exotherm from 20° C. to 25° C. The reaction was stirred at 60° C. for 18 hours, after which it was filtered through a Celite® pad and the pad was rinsed with acetonitrile (20 mL). Water (20 mL) was added to the combined filtrates and the resulting mixture was concentrated to 10 mL. Water (20 mL) was added and the resulting mixture was again concentrated to 10 mL. The resulting suspension was stirred at 20° C. for 18 hours and filtered. The filter cake was rinsed with water (2×5 mL) and dried to afford the title compound as a brown solid (0.680 g, 69%).

Example 17

3-Chloro-1-(pyridine-3-yl)-1H-pyrazole-5-carboxylic acid hydrochloride (6e)

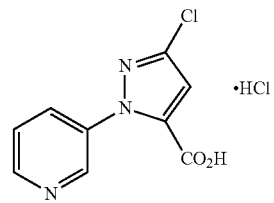 [SMILES: O=C(O)c1cc(Cl)nn1-c1cccnc1 ; Cl]

Methyl 3-chloro-1-(pyridin-3-yl)-1H-pyrazole-5-carboxylate (3.83 g, 16.1 mmol) was stirred in dioxane (53.7 mL). The orange suspension was heated until a solution was achieved. Lithium hydroxide hydrate (1.01 g, 24.2 mmol) in water (26.9 mL) was added to afford a darker red solution. The reaction was stirred at room temperature for 1 hours, at which point LCMS showed the corresponding acid to be the major product. The orange mixture was concentrated to dryness and the residue was mixed with 4 N hydrochloric acid in dioxane (100 mL). The suspension was heated to reflux for 1 h and allowed to cool to room temperature. The resulting suspension was filtered and the filter cake was rinsed with dioxane. The solid was vacuum dried at 50° C. to afford the desire product as a white solid (4.00 g, 91%): mp 244-246° C.; $^1$H NMR (400 MHz, DMSO-$d_6$) δ 9.00 (dd, J=2.5, 0.7 Hz, 1H), 8.82 (dd, J=5.2, 1.4 Hz, 1H), 8.35 (ddd, J=8.3, 2.4, 1.4 Hz, 1H), 7.85 (ddd, J=8.3, 5.2, 0.7 Hz, 1H), 7.25 (s, 1H); $^{13}$C NMR (101 MHz, DMSO-$d_6$) δ 158.71, 146.00, 143.44, 140.36, 137.00, 136.83, 125.19, 111.71; ESIMS m/z 224 ([M+H]$^+$).

Alternate Synthetic Route to: 3-Chloro-1-(pyridine-3-yl)-1H-pyrazole-5-carboxylic acid hydrochloride Methyl 3-chloro-1-(pyridin-3-yl)-1H-pyrazole-5-carboxylate (1.5 g, 6.0 mmol) was stirred in concentrated hydrochloric acid (25 mL). The reaction mixture was heated at reflux to afford a yellow solution. After heating overnight a solid had precipitated, and LCMS analysis of the mixture indicated that the reaction was complete. The mixture was allowed to cool to room temperature and dioxane (50 mL) was added. The mixture was concentrated to dryness. acetonitrile (50 mL) was added and the resulting mixture was concentrated. The residue was vacuum dried at 40° C. to afford the desired product as a yellow solid (1.6 g, 97%).

Example 18

Ethyl 5-oxo-2-(pyridin-3-yl)pyrazolidine-3-carboxylate

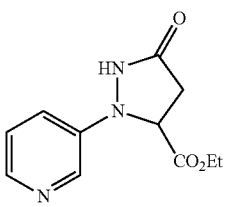 [SMILES: CCOC(=O)C1CC(=O)NN1c1cccnc1]

A 4-neck round bottomed flask (250 mL) was charged with sodium ethoxide (21 wt % in ethanol, 56 mL, 192 mmol). 3-Hydrazinopyridine.dihydrochloride (10.0 g, 55.0 mmol) was added, causing an exotherm from 20° C. to 32° C. The reaction was allowed to cool to 20° C. and diethyl maleate (13.4 mL, 82.0 mmol) was added, and the reaction was heated at 60° C. for 3 hours. The reaction was cooled to 20° C. and quenched with acetic acid. The reaction mixture was diluted with water (100 mL) and extracted with ethyl acetate (3×100 mL). The combined organics were concentrated to dryness and the residue was purified by flash column chromatography using ethyl acetate as eluent to the title compound as a blue oil (6.60 g, 51%): $^1$H NMR (400 MHz, DMSO-$d_6$) δ 10.40 (s, 1H), 8.40-8.26 (m, 1H), 8.19 (dd, J=4.4, 1.6 Hz, 1H), 7.47-7.21 (m, 2H), 4.77 (dd, J=9.8, 2.1 Hz, 1H), 4.22 (qd, J=7.1, 1.7 Hz, 2H), 3.05 (dd, J=17.0, 9.8 Hz, 1H), 1.99 (s, 1H), 1.25 (t, J=7.1 Hz, 3H); $^{13}$C NMR (101 MHz, DMSO-$d_6$) δ 170.37, 146.60, 142.60, 137.28, 123.54, 121.94, 65.49, 61.32, 32.15, 20.72, 13.94; ESIMS m/z 236 ([M+H]$^+$).

Example 19

Ethyl 3-chloro-1-(pyridin-3-yl)-4,5-dihydro-1H-pyrazole-5-carboxylate

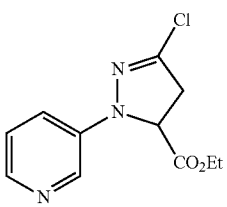 [SMILES: CCOC(=O)C1CC(Cl)=NN1c1cccnc1]

A 3-neck round bottomed flask (100 mL) was charged with ethyl 5-oxo-2-(pyridin-3-yl)pyrazolidine-3-carboxylate (8.50 g, 36.1 mmol) and acetonitrile (40 mL). Phosphoryl trichloride (4.05 mL, 43.4 mmol) was charged and the reaction was heated at 60° C. for 2 hours. The reaction was cooled to 20° C. and water (100 mL) was added. Sodium carbonate was added to adjust pH to 8 and the mixture was extracted with ethyl acetate (3×100 mL). The organic layers were concentrated to dryness and the residue was purified by flash column chromatography using 30-80% ethyl acetate/hexanes as eluent to provide the title compound as a yellow oil (7.30 g, 79%): $^1$H NMR (400 MHz, CDCl$_3$) δ 8.30 (dd, J=2.9, 0.8 Hz, 1H), 8.17 (dd, J=4.7, 1.4 Hz, 1H), 7.38 (ddd, J=8.4, 2.8, 1.4 Hz, 1H), 7.18 (ddd, J=8.4, 4.7, 0.7 Hz, 1H), 4.79 (dd, J=12.4, 6.9 Hz, 1H), 4.24 (qd, J=7.1, 1.1 Hz, 2H), 3.55 (dd, J=17.7, 12.4 Hz, 1H), 3.33 (dd, J=17.8, 6.9 Hz, 1H), 1.25 (t, J=7.1 Hz, 3H); $^{13}$C NMR (101 MHz, CDCl$_3$) δ 169.65, 141.90, 141.33, 141.09, 135.13, 123.53, 120.37, 62.89, 62.35, 42.45, 14.03; ESIMS m/z 254 ([M+H]$^+$).

Example 20

Ethyl 3-chloro-1-(pyridin-3-yl)-1H-pyrazole-5-carboxylate

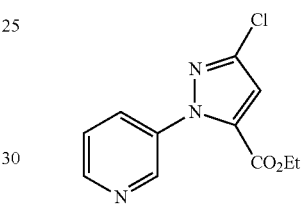

A 3-neck round bottomed flask (100 mL) was charged with ethyl 3-chloro-1-(pyridin-3-yl)-1H-dihydropyrazole-5-carboxylate (2.00 g, 7.88 mmol) and acetonitrile (20 mL). Manganese (IV) oxide (3.43 g, 39.4 mmol) was added, causing an exotherm from 20° C. to 21° C. The reaction was stirred at 60° C. for 18 hours. Additional manganese (IV) oxide (3.43 g, 39.4 mmol) was added and the reaction was stirred at 80° C. for 6 hours. The mixture was filtered through a Celite® pad and the pad was rinsed with ethyl acetate (20 mL). The combined filtrates were concentrated to dryness and the residue was purified by flash column chromatography using 10-60% ethyl acetate/hexanes. The pure fractions were concentrated to dryness to afford a white solid after drying (1.84 g, 93%): $^1$H NMR (400 MHz, CDCl$_3$) δ 8.75-8.64 (m, 2H), 7.79 (ddd, J=8.2, 2.6, 1.5 Hz, 1H), 7.42 (ddd, J=8.2, 4.8, 0.8 Hz, 1H), 6.98 (s, 1H), 4.27 (q, J=7.1 Hz, 2H), 1.27 (t, J=7.1 Hz, 3H); $^{13}$C NMR (101 MHz, CDCl$_3$) δ 157.90, 149.88, 147.01, 141.41, 136.24, 135.27, 133.34, 123.11, 111.97, 61.87, 13.98; ESIMS m/z 252 ([M+H]$^+$).

Alternate Synthetic Route to: Ethyl 3-chloro-1-(pyridin-3-yl)-1H-pyrazole-5-carboxylate A vial (20 mL) was charged with ethyl 3-chloro-1-(pyridin-3-yl)-1H-dihydropyrazole-5-carboxylate (0.500 g, 1.97 mmol) and acetonitrile (5 mL). Sodium persulfate (0.799 g, 2.96 mmol) was added, followed by sulfuric acid (0.733 g, 7.88 mmol) (An exotherm was observed). The reaction was heated at 60° C. for 18 hours. The reaction was cooled to 20° C. and poured into water (20 mL). The mixture was basified with sodium carbonate to pH 9 and extracted with ethyl acetate (2×20 mL). The organic layers were concentrated to a residue, which was purified by flash column chromatography using 50% ethyl acetate/hexanes as eluent to provide the title compound as a white solid (0.280 g, 56%).

Example PE-1

Prophetic preparation of (2,2-difluorocyclopropyl)methanethiol

To a solution of 2-(bromomethyl)-1,1-difluorocyclopropane (about 1 eq) in a solvent, such as methanol (at a concentration ranging from about 0.01 M to about 1 M), at temperatures between about 0° C. and about 40° C. may be added thioacetic acid (about 1 equivalents to about 2 equivalents), and a base, such as potassium carbonate (about 1 equivalent to 2 equivalents). An additional amount of a base, such as potassium carbonate (about 1 equivalent to 2 equivalents) may be added after a time ranging from about 30 minutes to 2 hours to the mixture to remove the acyl group. The reaction may be stirred until it is determined to be complete. The product may then be obtained using standard organic chemistry techniques for workup and purification.

Alternative Prophetic Preparation of: (2,2-Difluorocyclopropyl)methanethiol

To a solution of 2-(bromomethyl)-1,1-difluorocyclopropane (about 1 eq) in a solvent, such as methanol (at a concentration ranging from about 0.01 M to about 1 M), at temperatures between about 0° C. and about 40° C. may be added thioacetic acid (about 1 equivalent to about 2 equivalents), and a base, such as potassium carbonate (about 1 equivalent to 2 equivalents). The intermediate thioester product may then be obtained using standard organic chemistry techniques for workup and purification. To the thioester (about 1 equivalent) in a solvent, such as methanol (at a concentration ranging from about 0.01 M to about 1 M), at temperatures between about 0° C. and about 40° C. may be added a base, such as potassium carbonate (about 1 equivalent to 2 equivalents). The reaction may be stirred until it is determined to be complete. The product may then be obtained using standard organic chemistry techniques for workup and purification.

COMPARATIVE EXAMPLES

Example CE-1

Oxidation of 3-(3-chloro-4,5-dihydro-1H-pyrazol-1-yl)pyridine (5a) to 3-(3-chloro-1H-pyrazol-1-yl)pyridine (5b) using iron (III) chloride

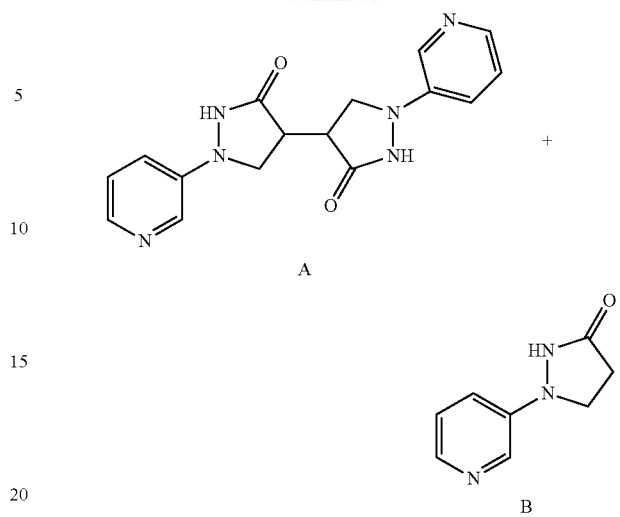

To a clear brown solution of 3-(3-chloro-4,5-dihydro-1H-pyrazol-1-yl)pyridine (0.480 g, 3.65 mmol) in dry N,N-dimethylformamide (5.4 mL) in a round bottomed flask (25 mL) was added anhydrous iron (III) chloride (0.215 g, 1.33 mmol, 0.5 eq.) leading to a dark brown solution. Dried air was bubbled through the mixture via a Teflon tube. The mixture was stirred at 100° C. for 19 hours and cooled down to 40° C. LC-MS indicated disappearance of starting material along with significant amount (>50%) of side products from α-dimerization (A): ESIMS m/z 325 ([M+H]$^+$), and hydrolysis (B): ESIMS m/z 164 ([M+H]$^+$) of starting material. The mixture was concentrated under vacuum and the residue was purified by flash column chromatography using 0-60% ethyl acetate/hexanes as eluent to afford product that contains N,N-dimethylformamide. After drying under high vacuum for 16 hours, the title compound was obtained as a brown solid (0.164 g, 35%).

LC-MS Conditions: Phenomenex Kinetex C$_{18}$ column, 40° C., 1 μL injection; 1 mL/min flow; 95% water (0.1% formic acid)/5% acetonitrile (0.05% formic acid), gradient to 50% acetonitrile (0.05% formic acid) over 15 min., 3 min. post time. t$_r$(B)=2.18 min, t$_r$(A)=5.16 min, t$_r$(product)=6.27 min.

Example CE-2

Oxidation of 3-(3-chloro-4,5-dihydro-1H-pyrazol-1-yl)pyridine (5a) to 3-(3-chloro-1H-pyrazol-1-yl)pyridine (5b) using iron (III) chloride

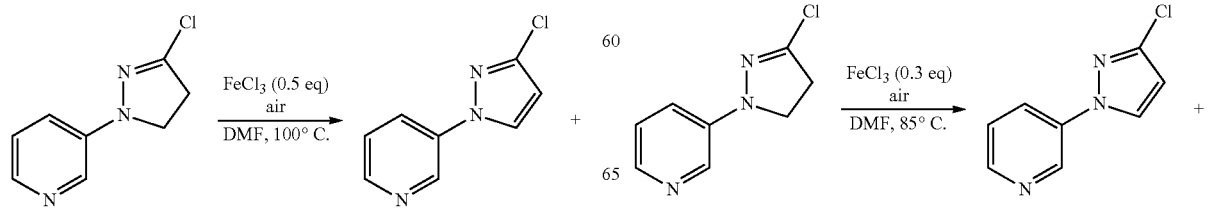

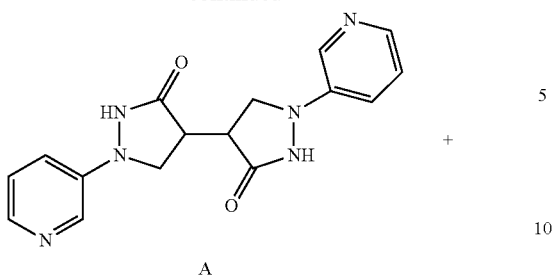

A

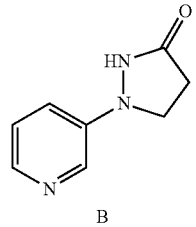

B

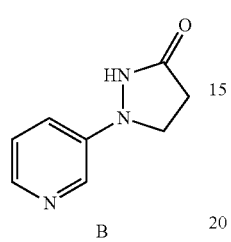

B

To a solution of 3-(3-chloro-4,5-dihydro-1H-pyrazol-1-yl)pyridine (0.543 g, 3.00 mmol) in dry N,N-dimethylformamide (6.0 mL) in a round bottomed flask (25 mL) was added anhydrous iron (III) chloride (0.146 g, 0.900 mmol, 0.3 eq.) leading to a dark brown solution. The mixture was stirred at 85° C. when dried air was bubbled through the mixture via a Teflon tube. LC-MS indicated 7.3% conversion into desired product along with 20% conversion into dimeric side product (A) at 3.5 hours. After 22 hours, LC-MS indicated 9.6% conversion into desired product along with 22% conversion into dimeric side product (A). The reaction was stopped and no further isolation was performed.

Example CE-3

Oxidation of 3-(3-chloro-4,5-dihydro-1H-pyrazol-1-yl)pyridine (5a) to 3-(3-chloro-1H-pyrazol-1-yl)pyridine (5b) using catalytic copper (I) chloride

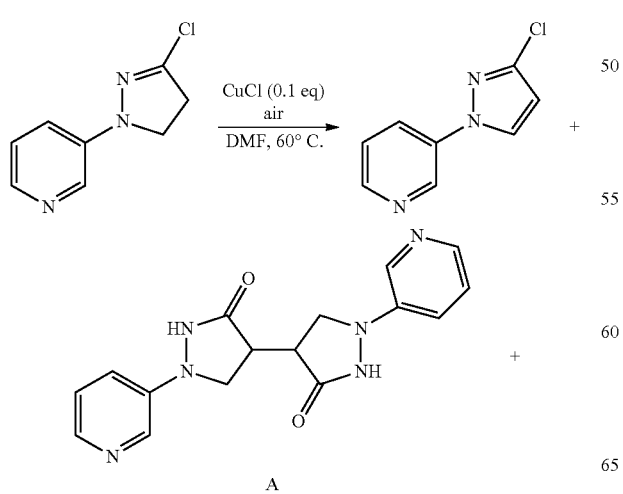

A

To a solution of 3-(3-chloro-4,5-dihydro-1H-pyrazol-1-yl)pyridine (0.543 g, 3.00 mmol) in dry N,N-dimethylformamide (3.0 mL) in a round bottomed flask (10 mL) was added copper (I) chloride (0.300 g, 0.300 mmol, 0.1 eq.) leading to a green suspension. Dried air was bubbled through the mixture. The resultant dark green mixture was stirred at 60° C. for 18 hours and LC-MS indicated 1.8% conversion into desired product along with 0.7% conversion into dimeric side product (A). The mixture was not purified.

Example CE-4

Oxidation of 3-(3-chloro-4,5-dihydro-1H-pyrazol-1-yl)pyridine (5a) to 3-(3-chloro-1H-pyrazol-1-yl)pyridine (5b) using catalytic copper (I) chloride

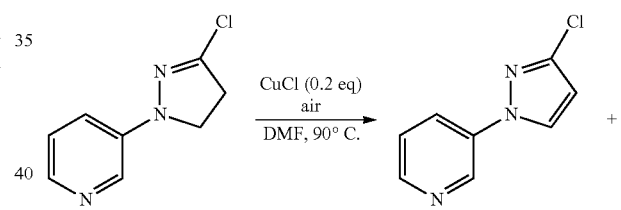

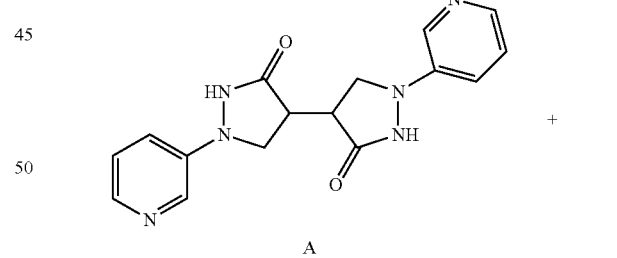

A

B

To a solution of 3-(3-chloro-4,5-dihydro-1H-pyrazol-1-yl)pyridine (0.543 g, 3.00 mmol) in dry N,N-dimethylformamide (3.0 mL) in a round bottomed flask (10 mL) was added anhydrous copper (I) chloride (0.0590 g, 0.600 mmol, 0.2 eq.) leading to a dark green suspension. The mixture was stirred at 90° C. when dried air was bubbled through via a Teflon tube. The solution turned dark brown and LC-MS indicated 31% conversion into desired product along with 8.3% conversion into dimeric side product (A) at 16 hours. After 22 hours, LC-MS indicated 35% conversion into desired product along with 8.5% conversion into dimeric side product (A). The reaction was stopped and no further isolation was performed.

Example CE-5

Oxidation of 3-(3-chloro-4,5-dihydro-1H-pyrazol-1-yl)pyridine (5a) to 3-(3-chloro-1H-pyrazol-1-yl)pyridine (5b) using potassium persulfate in acetonitrile

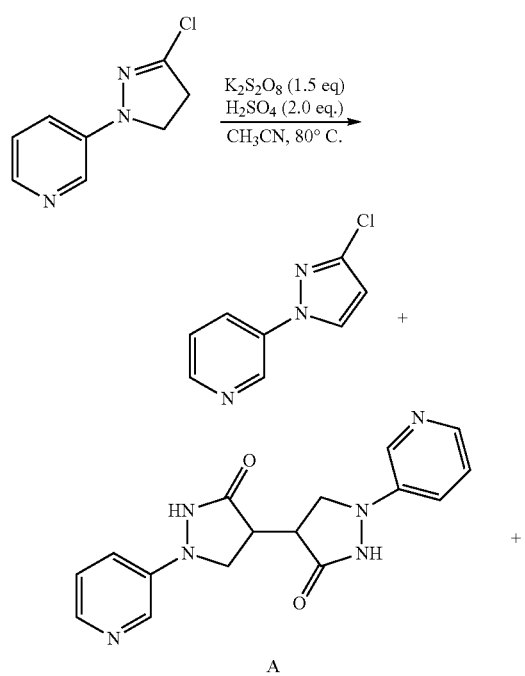

To a solution of 3-(3-chloro-4,5-dihydro-1H-pyrazol-1-yl)pyridine (0.181 g, 1.00 mmol) in dry acetonitrile (3.0 mL) in a round bottom flask (10 mL) was added potassium persulfate (0.405 g, 1.50 mmol, 1.5 eq.). The mixture was cooled in an ice-water bath. Sulfuric acid (conc., 0.106 mL, 2.00 mmol, 2.0 eq.) was added slowly and the mixture was stirred at 80° C. for 6 hours. Sticky brown solid was formed at the bottom of the flask and contained mostly starting material by LC-MS. LC-MS of the solution indicated only starting material and no conversion into desired product.

Example CE-6

Alkylation Versus Retro-Michael-Like Decomposition

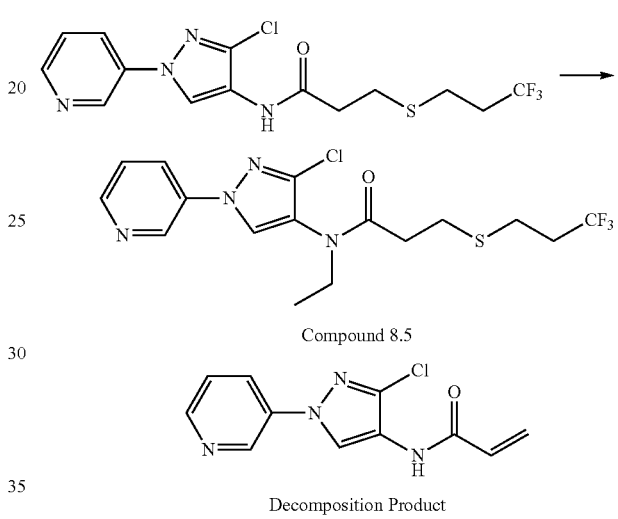

Compound 8.5

Decomposition Product

A suspension of sodium hydride (60% in oil, 1.03 eq) and solvent (1 vol) was stirred for 5 minutes. N-(3-Chloro-1-(pyridin-3-yl)-1H-pyrazol-4-yl)-3-((3,3,3-trifluoropropyl)thio)propanamide (1 eq) dissolved in solvent (2 vol) was slowly added dropwise over 5 minutes. Ethyl bromide (3.3 eq) and additive (0.22 eq) were added sequentially. The suspension was then allowed to stir at room temperature until consumption of starting material was observed. The selectivity of Compound 6.3 over the decomposition product was determined by HPLC (See Table 2).

TABLE 2

| Entry | Additive | Solvent | Time (hours) | Compound 8.5:Decomposition Product |
|---|---|---|---|---|
| 1 | tetrabutyl-ammonium iodide | N,N-dimethylformamide | 24 | 81:19 |
| 2 | potassium iodide | N,N-dimethylformamide | 72 | 94:6 |
| 3 | potassium iodide | N-methylpyrolidinone | 20 | 92:8 |

Example CE-7

3-Chloro-N-ethyl-1-(pyridin-3-yl)-1H-pyrazol-amine

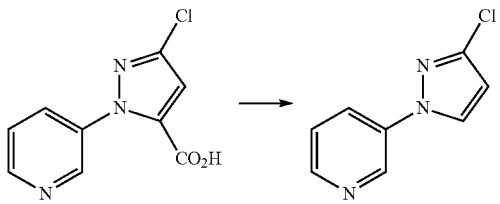 [SMILES: O=C(O)c1cc(Cl)nn1-c1cccnc1 ; Clc1ccn(-c2cccnc2)n1]

Attempted Decarboxylation with Sulfuric Acid:

3-Chloro-1-(pyridin-3-yl)-1H-pyrazole-5-carboxylic acid hydrochloride (1.00 g, 2.50 mmol) was dissolved in warm sulfolane (12.5 mL). sulfuric acid (1.35 mL, 25.0 mmol) was added and the reaction mixture was heated to 100° C. After stirring for 1 hour, LCMS indicated that the reaction did not occur. The reaction was further heated at 130° C. for 2 hours, at which point LCMS indicated no change. Additional sulfuric acid (4 mL) was added and the reaction was heated at 150° C. for 2 hours, at which point LCMS showed a new major peak that did not correspond to desired product.

Attempted Decarboxylation with Palladium (II) Trifluoroacetate/Trifluoroacetic Acid:

3-Chloro-1-(pyridin-3-yl)-1H-pyrazole-5-carboxylic acid hydrochloride (1.00 g, 2.50 mmol) was dissolved in a mixture of dimethylsulfoxide (0.625 mL) and N,N-dimethylformamide (11.9 ml). Trifluoroacetic acid (1.93 ml, 25.0 mmol) was added followed by the addition of palladium(II) trifluoroacetate (0.332 g, 1.00 mmol). The reaction was heated at 100° C. overnight, at which time LCMS indicated that a reaction had occurred but no desired product had been formed.

BIOLOGICAL EXAMPLES

Example A

Bioassays on Green Peach Aphid ("GPA") (*Myzus persicae*) (MYZUPE.)

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four posts with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

Corrected % Control=100*(X−Y)/X where
X=No. of live aphids on solvent check plants and
Y=No. of live aphids on treated plants The results are indicated in the table entitled "Table 1: GPA (MYZUPE) and sweetpotato whitefly-crawler (BEMITA) Rating Table".

Example B

Bioassays on Sweetpotato Whitefly Crawler (*Bemisia tabaci*) (BEMITA.)

The sweetpotato whitefly, *Bemisia tabaci* (Gennadius), has been recorded in the United States since the late 1800s. In 1986 in Florida, *Bemisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective insecticides.

Cotton plants grown in 3-inch pots, with 1 small (3-5 cm) true leaf, were used at test substrate. The plants were placed in a room with whitely adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Pesticidal activity was measured by using Abbott's correction formula (see above) and presented in Table 1.

TABLE 1

GPA (MYZUPE) and sweetpotato whitefly-crawler (BEMITA) Rating Table

| Example Compound | BEMITA | MYZUPE |
|---|---|---|
| 5a | B | B |
| 5e | A | A |
| Compound 5.5 | B | A |
| Compound 8.5 | A | A |
| Compound 9.5 | A | A |

| % Control of Mortality | Rating |
|---|---|
| 80-100 | A |
| More than 0-Less than 80 | B |
| Not Tested | C |
| No activity noticed in this bioassay | D |

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A process comprising alkylating pesticidal thioether (3b)

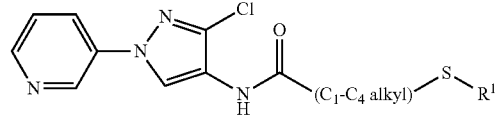

(3b)

with $R^2$—$X^2$ in the presence of cesium carbonate and a polar solvent, to yield pesticidal thioether (3c),

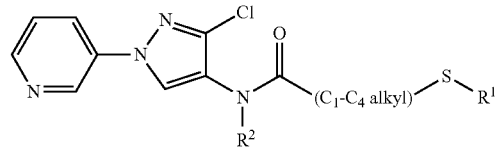

(3c)

wherein,
$X^2$ is a leaving group,
$R^1$ is selected from the group consisting of $C_1$-$C_4$-haloalkyl and $C_1$-$C_4$-alkyl-$C_3$-$C_6$-halocycloalkyl, and
$R^2$ is selected from the group consisting of $C_1$-$C_4$-alkyl.

2. The process of claim 1, wherein $X^2$ is halo, mesylate, or tosylate.

3. The process of claim 1, wherein $R^2$ is methyl, ethyl or propargyl.

4. The process of claim 1, wherein $R^2$—$X^2$ is selected from the group consisting of methyl iodide, ethyl bromide, ethyl iodide, propargyl chloride, propargyl bromide, ethyl mesylate, propargyl mesylate, ethyl tosylate and propargyl tosylate.

5. The process of claim 1, wherein the polar solvent is N,N-dimethylformamide.

* * * * *